US006365050B1

(12) United States Patent
Cauchon

(10) Patent No.: US 6,365,050 B1
(45) Date of Patent: Apr. 2, 2002

(54) METHOD FOR STOPLESS AND SPLITLESS FLOW FIELD-FLOW FRACTIONATION

(75) Inventor: Gregory Paul Cauchon, Thousand Oaks, CA (US)

(73) Assignee: Amgen Inc., Thousand Oaks, CA (US)

( * ) Notice: Subject to any disclaimer, the term of this patent is extended or adjusted under 35 U.S.C. 154(b) by 0 days.

(21) Appl. No.: 09/643,517

(22) Filed: Aug. 22, 2000

(51) Int. Cl.[7] ............................................... B01D 15/08
(52) U.S. Cl. ...................... 210/635; 210/656; 210/748; 210/198.2; 210/800; 210/804; 209/18; 209/131; 209/156; 209/422
(58) Field of Search ................................ 210/635, 656, 210/695, 748, 243, 800, 804, 511, 513, 198.2; 209/18, 131, 156, 422

(56) References Cited

U.S. PATENT DOCUMENTS

| | | | |
|---|---|---|---|
| 3,449,938 A | | 6/1969 | Giddings .................... 73/23 |
| 4,147,621 A | | 4/1979 | Giddings ................... 210/143 |
| 4,214,981 A | | 7/1980 | Giddings ................... 209/155 |
| 4,657,676 A | * | 4/1987 | Keary ..................... 210/198.2 |
| 4,737,268 A | | 4/1988 | Giddings ................... 210/748 |
| 4,830,756 A | | 5/1989 | Giddings ................... 210/748 |
| 4,894,146 A | | 1/1990 | Giddings ................... 210/748 |
| 5,039,426 A | | 8/1991 | Giddings ................... 210/695 |
| 5,141,651 A | | 8/1992 | Giddings ................... 210/748 |
| 5,160,625 A | * | 11/1992 | Jonsson ................... 210/635 |
| 5,193,688 A | | 3/1993 | Giddings ................... 210/748 |
| 6,109,119 A | * | 8/2000 | Jiang ....................... 210/511 |
| 6,180,906 B1 | * | 1/2001 | Trainoff ................... 210/748 |

OTHER PUBLICATIONS

P. Schettler, "Field–Flow Fraction—A Versatile Tool for Particle Separation and Characterization", LC–GC, vol. 14(10), pp. 852–859, (1996).
J. Giddings et al., "Separation of Water Soluble Synthetic and Biological Macromolecules by Flow Field–Flow Fractionation", *Polymer Materials Science Engineering*, vol. 65, pp. 21–23 (1991).
Liu et al., "Hydrodynamic Relaxation in Flow Field–Flow Fractionation Using Both Split and Frit Inlets", *Analytical Chemistry*, vol. 63, pp. 2115–2122, (1991).

* cited by examiner

*Primary Examiner*—Ernest G. Therkorn
(74) *Attorney, Agent, or Firm*—Craig A. Crandall; Ron K. Levy; Steven M. Odre

(57) ABSTRACT

An improved flow field-flow fractionation (flow FFF) process has been developed which permits the high-resolution separation of analytes without stopping or reversing the axial flow, introducing additional axial flow streams, or further splitting the axial flow stream. The improved procedure speeds up, streamlines, and simplifies the apparatus and the procedure without unduly concentrating the sample, permits the use of flow-sensitive detection technologies in a manner which has previously been difficult or impossible, and avoids the artifactual aggregation which is known to result from other relaxation procedures. The process also permits the calculation of the channel width w without reference to system or void peaks in the fractogram. These capabilities render the improved flow FFF procedure more accurate as well as more practical, and permit automated flow FFF separations to be routinely performed on commercially-available HPLC systems with only minor modifications.

11 Claims, 11 Drawing Sheets

METHOD FOR STOPLESS AND SPLITLESS FLOW FIELD-FLOW FRACTIONATION

FIELD OF THE INVENTION

This invention relates generally to a method for performing flow field-flow fractionation (flow FFF), which is useful in the separation, isolation, and characterization of a wide range of particles and macromolecules.

BACKGROUND OF THE INVENTION

There is a tremendous need in virtually all branches of science and technology for the separation and characterization of a wide variety of analytes. Although numerous methods have been devised to accomplish such separations, including various forms of chromatography, filtration, precipitation, electrophoresis, and centrifugation, no one technique is universally applicable. One useful family of techniques is field-flow fractionation (FFF), as taught by J. Giddings in U.S. Pat. No. 3,449,938 and recently reviewed by P. Schettler, $LC$-$GC$ 14(10), 852 (1996), which are incorporated by reference herein. The most universally applicable of these FFF techniques is flow field-flow fractionation (flow FFF), as taught by J. Giddings in U.S. Pat. No. 4,147,621, which is incorporated by reference herein. Flow FFF devices effect the fractionation of particles by pushing an analyte contained in the "channel flow" stream (symbolized herein as '$V_z$') axially along the surface of a filtration membrane inside a narrow channel while simultaneously pushing a "cross flow" stream (symbolized herein as '$V_x$') through the channel in a direction orthogonal to the channel flow stream $V_z$. Inside the channel, these two flowstreams intersect and intermingle, and the crossflow stream $V_x$ provides a field of hydraulic force across the planar surface of the filtration membrane which is sufficient to permit the separation of analyte samples into their constituent components based on differences in their hydrodynamic sizes or diffusion coefficients. The crossflow stream thus provides a force field which results in the retention of the analyte. Larger analytes feel or sense the force of this crossflow stream more strongly, due to their larger Stokes radii, and therefore spend their time, on average, closer to the filtration membrane. Smaller analytes feel the crossflow stream more weakly, and diffuse away from the filtration membrane to occupy a higher average position over it, where they encounter the faster flowstreams of the Poiseuille flow velocity distribution under laminar channel flow conditions and are carried along the channel faster and elute as a peak sooner than larger analytes. In this way, the analyte particles are fractionated as a function of their diffusion coefficients or apparent hydrodynamic sizes.

Many publications, such as J. Giddings et al., *Polym. Mater. Sci. Eng.* 65, 21 (1991), P. Schettler, *LC-GC* 14(10), 852 (1996), J. Giddings, *Sep. Sci. Technol.* 24(9&10), 755 (1989), J. Giddings et al., *Meth. Biochem. Anal.* 26, 79 (1980), F. Yang et al., *Anal. Chem.* 49(4), 659 (1977), and M.-K. Liu et al.,*Anal. Chem.* 63, 2115 (1991), and a number of patents, such as U.S. Pat. Nos. 4,214,981, 4,737,268, 4,830,756, 4,894,146, 5,039,426, 5,141,651, and 5,193,688, all of which are incorporated by reference herein, have disclosed applications, modifications, calibration procedures, and improvements to the flow FFF separation process, so that the set of conditions which are classically employed in flow FFF systems is well known and fully illustrated in the prior art.

One important advantage of flow FFF is the number and variety of the variables which are available in the design of channels and the operating parameters. For example, although thin, planar channels are the most common, an annular channel geometry is also known, as illustrated in FIG. 7 of U.S. Pat. No. 4,214,981. In addition, at least three different "operating modes" are known for flow FFF, including the "normal," "steric," and "hyperlayer" modes. In the normal mode, the analyte exists predominantly as a "cloud" of particles hovering over the surface of the membrane, balanced between the crossflow force driving it towards the accumulation wall on the one hand and diffusion, flow-induced lift forces, and steric effects on the other hand, driving the analyte away from the accumulation wall during its travel down the channel. In this normal mode, which takes place with small particles at modest flow rates, the contribution of flow-induced lift forces is considered to be minimal, so that the primary forces acting on the particles are the hydraulic crossflow force field and the back-diffusion of the analyte away from the filtration membrane. Thus, in normal mode, smaller particles elute before larger particles. In the steric mode, which predominates for larger particles and relatively high crossflow velocities, the particles essentially reside along the surface of the filtration membrane, so that larger analyte particles protrude further into the channel and sample the faster flowstreams of the Poiseuille flow velocity distribution. Thus, in steric mode the particles are considered to essentially "roll" along the surface of the filtration membrane, so that the elution order is the reverse of that observed for normal mode, with larger particles eluting before smaller ones. In hyperlayer mode, which takes place with similar larger particles as required for the steric mode but with somewhat faster flow velocities, the flow-induced lift forces which are considered to be minimal in normal mode become significant, and lead to a fluid force lifting the particles off from the surface of the membrane and into a relatively narrow layer of fluid. As with steric mode, larger particles in hyperlayer mode elute before smaller particles.

In addition, there also exist at least two configurations of flow FFF channel. In "symmetrical" flow FFF configuration, the crossflow stream $V_x$ enters the channel from the crossflow inlet frit above it and passes through the channel and then through the filtration membrane, whereupon retained analyte is removed from the cross flow and the remaining $V_x$ stream exits through the outlet frit underneath the filtration membrane. In symmetrical flow FFF, the channel flow stream $V_z$ is thus physically distinct from the cross flow stream $V_x$, and these two flow streams are typically "balanced" by independently adjusting the four flow streams $V_z$in, $V_z$out, $V_x$in, and $V_x$out by any convenient means until $V_z$in equals $V_z$out and $V_x$in equals $V_x$out. However, these two flow streams need not be balanced in this manner, since the only physical requirement is that the total of the sum of $V_z$in and $V_x$in is equal to the total of the sum of $V_z$out and $V_x$out. Thus, symmetrical flow FFF channels can also be operated in "unbalanced flow" mode, in which the relative velocities of the four flow flowstreams can be adjusted to obtain any desired effect. In "asymmetrical" flow FFF, the crossflow inlet frit is replaced with a non-porous solid material, so that the channel flow stream $V_z$in and the crossflow stream $V_x$in must be mixed and pumped into the channel together through a single channel flow inlet. Typically, the total input flux is chosen in advance, and the ratio of the fluid flow which exits from the channel flow outlet to that which exits through the filtration membrane and the crossflow outlet can be controlled by any convenient means, including pieces of constrictive tubing, pressure regulators, etc. In this way, the desired degree of retention can be achieved.

The flow FFF channel can also contain one of a number of potential channel spacer "geometries," typically produced by cutting a portion out from the center of a thin sheet of spacer material, most often a plastic. For example, if a portion of the spacer consisting of a rectangle 2.0 cm wide by 25 cm long and bearing end-pieces consisting of isosceles triangles 2.0 cm on a side is removed, and the apparatus assembled, then the channel would exhibit a "parallel-walled" geometry. Similarly, a triangular portion of 2.0 cm breadth and 20 cm length contiguous to an isosceles triangles portion 2.0 cm on a side would yield a geometry referred to as "tapered-wall." Although a large number of such geometries are possible, the parallel-walled and tapered-wall, in combination with various end-piece geometries, are the most common.

These two possible channel forms, three modes of flow FFF, two types of flow FFF channel, and large number of potential channel geometries are all independent and non-exclusive, and can exist in almost any combination. For example, a thin planar channel form with an inlet frit operated at modest flow rates with small analyte particles can be described as a planar symmetrical normal-mode parallel-walled separation, while an annular channel form with a solid internal core, a single, combined channel flow and crossflow inlet, and a filtration membrane supported by the outside frit operated at high flow rates with large analyte particles can be described as an annular asymmetrical steric-mode separation. All of these potential combinations are apparent to those skilled in the art.

Although it is in principle applicable to a wide variety of analytes, flow FFF has met with only modest commercial success, in comparison with related techniques such as size-exclusion chromatography (SEC). This lack of success is due primarily to the inherent limitations of the existing methodology and instrumentation, which include strong and unpredictable interactions with membranes, poor resolution, and especially the peculiar requirements resulting from the need for relaxing the analyte sample prior to commencing the fractionation, as described more fully below.

Flow FFF separations both cause and require the analyte to be in an equilibrium position against the filtration membrane, balanced between the crossflow force driving it towards the filtration membrane on the one hand and diffusion, flow-induced lift forces, and steric effects on the other hand, driving the analyte away from the filtration membrane during its travel down the channel. However, when the analyte sample is first introduced into the channel, it is distributed essentially evenly over the entire incoming cross-sectional area, far from the desired equilibrium distribution against the filtration membrane, as described more fully in M.-K. Liu et al., *Anal. Chem.* 63, 2115 (1991). After introduction of the analyte sample into the channel, the analyte will relax to its equilibrium distribution close to the filtration membrane under the influence of the crossflow field which drives the flow FFF separation. In order to accomplish a flow FFF separation of reasonable resolution, the relaxation of this incoming analyte must be occur before it is pushed any significant distance axially along the membrane's surface by the channel flow. That is, continuing the channel flow during this period of crossflow relaxation leads to unacceptably broadened analyte peaks, since the widely-varying flowrates of the different laminae across the incoming cross-sectional area will deposit the analyte in a very broad pattern onto the filtration membrane.

Although it has long been presumed (see e.g. J. Giddings et al., *Meth. Biochem. Anal.* 26, 79 (1980)) that a sufficiently large field, with its resulting increased retention of the analyte, combined with a decreased channel thickness and a low channel flow velocity would attenuate this relaxational broadening, it has never been possible to make the relaxation effect negligible in flow FFF. For this reason, as described for example by F. Yang et al., *Anal. Chem.* 49, 659 (1977), and by Liu et al. in *Anal. Chem.* 63, 2115 (1991), as well as in other references, the standard procedure in flow FFF has long been to stop the channel flow for a period of time which is sufficient to relax the analyte to its equilibrium position against the membrane, before continuing the flow FFF experiment. In this so-called "stop-flow" relaxation procedure, the analyte enters the channel via the axial or channel flowstream for a period of time which is estimated to be sufficient to remove all of the analyte from the inlet tubing and deposit it onto the channel. The channel flow ($V_z$) is then stopped in order to control band distortion and broadening, typically by moving a flow-switching valve, and the cross flow ($V_x$) is continued for a period of time which is estimated to be sufficient to establish the analyte in its equilibrium position with respect to the filtration membrane. This period of stopped flow is typically sufficient to allow 1–2 times the channel volume to pass through the channel in the cross flow, and usually requires between 5 seconds and several minutes (see, for example, the stop-flow time ($t_{sf}$) of 120 seconds required for DNA in FIG. 5 of J. Giddings et al., *Polym. Mater. Sci. Eng.* 65, 21 (1991)). After the stop-flow period, the axial flow is re-established, typically by returning the flow-switching valve to its original position, and the analyte is eluted from the channel. Thus, during this stop-flow relaxation process, analyte components which are distributed widely in the flowstream laminae entering the channel are forced into a narrow cross-sectional region close to the filtration membrane from which a reasonably efficient separation can take place. Failure to fully relax the sample prior to the fractionation experiment is known to result in a large degree of dispersive broadening of the analyte, leading to unacceptably poor resolution and preventing the sample components from being distinguished from one another.

Unfortunately, even in the best of cases, this so-called stop-flow procedure leads to flow instabilities and other problems which are manifest as baseline shifts and extraneous peaks. For example, one common problem with stop-flow relaxation is the presence of so-called "void peaks," which elute at or near the geometric void volume of the channel (see, for example, the large void peak in FIG. 2 of J. Giddings et al., *Polym. Mater. Sci. Eng.* 65, 21 (1991)). Furthermore, the stoppage of axial hydrodynamic motion over the surface of the membrane frequently leads to particle adhesion to the channel walls, and especially to the filtration membrane. The stop-flow procedure also increases the run time by at least the stop-flow period, and axial dispersion continues to take place during this stop-flow period, so that the peak continues to broaden while the relaxation is taking place. The hydraulic movements inside the channel during the stopping and restarting of the channel flow cause further disruption of the analyte zone, leading to additional band spreading and a loss of resolution. In addition, the stop-flow procedure renders very difficult the use of certain detectors, such as light-scattering (LS) and refractive-index (RI) detectors, which are sensitive to the pressure changes which invariably accompany flow-stream switching. In the case of LS detectors, the stop-flow procedure itself causes additional artifactual peaks to be detected, which appear to result at least in part from the removal of particles from the membrane and channel surfaces by the resulting hydraulic shock wave. Stop-flow relaxation also requires additional switching valves, tubing, and other components, as well as controlling software and signal pulses for the activation of the additional components, rendering the process more complicated and expensive. Thus, methods which require the stop-flow relaxation procedure result in excessive broadening of analyte peaks, compromise the effectiveness and utility of detectors which are among the most useful methods for characterizing fractionated species, and overly complicate and encumber the flow FFF process while increasing the cost.

Despite the many disadvantages of the stop-flow procedure, however, the system void peaks are useful in determining the void time $t_0$ and the void volume $V_0$ of the channel. The retention time $t_r$ of the true void peak (normally the second of the two early-eluting system peaks) is converted into a retention volume using the known channel flow rate $V_z$. From this volume is subtracted the total void volumes of the components immediately preceding the channel, including the injector, any valves, and the tubing. The difference yields the true void volume $V_0$ of the channel, which can be converted back to the true void time $t_0$ by dividing it by the channel flow rate $V_z$. These true void times and void volumes are useful in calculating the channel width w, from which many other parameters useful in the characterization of both the analyte sample, including the distribution of diffusion coefficients or frictional coefficients, and of the separation, including measures of the efficiency such as the height equivalent to a theoretical plate, the resolution, the fractionating power, and the selectivity, can be computed. To be most useful, any improved method which could eliminate the early-eluting system peaks observed with the stop-flow relaxation procedure should also be accompanied by a method for calculating either the channel void time $t_0$, the void volume $V_0$, or the channel width w which does not depend on identifying a discrete void peak in the fractogram.

The severe limitations of the stop-flow technique have long been recognized, and another technique, hydrodynamic relaxation, has resulted from attempts to avoid these pitfalls. Two variants of this technique, inlet splitting and frit inlets, are described more fully in M.-K. Liu et al., *Anal. Chem.* 63, 2115 (1991). In each of these methods, the analyte is driven close to its equilibrium position by a higher-velocity flow substream rather than by the lower-velocity crossflow field in the channel. In the frit-inlet method, disclosed more fully by Giddings in U.S. Pat. No. 5,193,688 and described in M.-K. Liu et al., *Prot. Sci.* 2, 1520 (1993), hydrodynamic relaxation is carried out by the introduction of an additional flowstream into the channel through an additional inlet frit near the entrance of the main axial flow bearing the analyte. This so-called "frit-inlet flow" enters the channel from a position near the inlet cross flow frit and, by virtue of its volume, pushes the existing contents (which enter the channel through the main axial entrance) towards the accumulation wall. In effect, this "relaxes" the analyte towards the membrane at a rate which is faster than the velocity of the crossflow field. Although this technique can work reasonably well for certain analytes, it has at least six important disadvantages. First, it is not generally applicable, and second, it often results in a loss of resolution as compared with the stop-flow relaxation method. Third, it requires the use of a separate flowstream, necessitating an additional pump (this is typically the third pump in the system). Fourth, the increased effective cross flow field under the inlet frit leads to increased and complicated adsorption of the analyte to the underlying membrane, requiring in the best case extensive calibration of the channel for each analyte and set of conditions. Fifth, frit inlet relaxation is known to cause artifactual aggregation of some analytes. Finally, the frit-inlet method also adds a large volume of solvent to the analyte, diluting it and rendering its subsequent detection and characterization more difficult.

In an effort to overcome the dilution of the analyte by an inlet frit, or to concentrate a dilute analyte as it emerges from the channel, an outlet frit can be added which is capable of stripping off the bulk liquid flowing above the sample layers in the channel. This outlet frit effectively concentrates the analyte components, aiding in their detection, characterization, or collection. Outlet frits suffer from some of the same problems which plague inlet frits, including a loss of resolution, and also introduce yet another flow stream, confounding the process of balancing the flow rates and unduly complicating the flow FFF procedure.

The latter difficulty can be mitigated somewhat by combining the outlet frit with an inlet frit to produce a channel architecture referred to as a 'frit inlet/frit outlet' system. If these two flow streams are independent, at least one additional pump is required for the inlet frit, although two additional pumps are sometimes used, and this flow stream also has to be taken into account when balancing the flow rates. The flowstreams from these two frits can be closed into a circle by routing the output of the outlet frit into the intake of a pump which then pumps the fluid into the inlet frit, somewhat simplifying the fluidic configuration, since the flowrates into and out of the respective frits are known and fixed. However, such a system still requires at a minimum one additional pump, and this circular pumping scheme also imposes impossible demands on the performance of that pump. The pump must produce smooth, pulseless flow out into the channel to preserve the laminar fluid flow required for flow FFF separations, and must also take the split frit out flow smoothly into its intake manifold, again without pressure fluctuations. At the present time, there is no commercially-available pump which completely fulfills these requirements, so that the use of the split inlet/outlet configuration must be confined to systems where low resolution and the use of only relatively pressure-insensitive (e.g. UV) detectors are acceptable. Specifically, frit inlet/frit outlet systems cannot be used quantitatively with LS detectors, and also cause RI detectors to perform poorly. Furthermore, outlet frits inevitably remove some small fraction of the analyte, and re-introducing this material into the inlet frit can lead to significant contamination of the incoming analyte and a reduction in the efficiency and resolution of the fractionation. Thus, frit inlet/frit outlet systems add undue difficulty and cost to the fractionation while also decreasing its resolution and efficiency and suffering from all of the deficiencies of frit inlet and frit outlet systems mentioned above.

In the alternative hydrodynamic relaxation technique, the inlet-splitter method, relaxation is carried out by the insertion of a thin flow splitter to divide the inlet region into two slit-like flow spaces. Manipulation of the flow rates of the incoming streams entering above and below the splitter, so as to obtain a neat carrier flow rate which is significantly greater than the flow rate of the sample-bearing stream, drives the latter into a thin laminus close to the accumulation wall of the channel, where it is close to its equilibrium position against the accumulation wall. However, there are several disadvantages to the use of such inlet splitters in flow FFF systems. First, of course, is the introduction of yet another flow stream. Second, for proper operation the inlet splitter must be suspended evenly across the several-centimeter-wide gap of the thin channel; unevenness of even a few tens of micrometers will noticeably distort the hydrodynamic relaxation process. A third difficulty is that the introduction of a flow splitter and the two associated flow spaces on either side of the splitter, yielding a total of three layers in all, is very often inconsistent with the utilization of very thin, high-performance FFF channels (e.g. channel widths of roughly 50–508 $\mu$m), Fourth, since the flow stream in which the sample is introduced must traverse the narrow gap on one side of the splitter, where the thickness is only a fraction of the full channel width, there is an enhanced risk that larger particles in the sample, whether part of the sample or an impurity therein, will clog all or part of the fluid path needed for sample introduction. Fifth, at high flowrates the abrupt change in flow direction at the splitter edges may introduce eddy currents in the fluid capable of disrupting the distribution of components near the inlet and outlet. Furthermore, this technique does not exhibit the same high resolution as other flow FFF relaxation methods, so that such split-inlet cells have been largely confined to continuous, binary separations (for example, the SPLITT channel illustrated in FIG. 2 of P. Schettler, *LC-GC* 14(10), 852 (1996)).

A fourth type of sample relaxation, reversed-flow focussing, is used almost exclusively in asymmetrical flow FFF due to the inability in this mode to independently control the channel and crossflow rates. It is, however, also compatible with the operation of symmetrical flow FFF channels. In reversed-flow focussing not only is the axial flow interrupted for a period of time, but the flow direction is actually reversed during the relaxation period. In order to accomplish this, the reversed flow passes backwards through at least the $V_z$ outlet from the channel, and the flow may even be reversed through one or more of the detectors. The two flows, entering from opposite ends of the channel, meet at a point determined by the relative volumetric flow rates of the two streams, whereupon all of the flow passes through the membrane and out of the channel through the crossflow outlet frit. Such a scheme is not possible for many fluorescence and RI detectors, which cannot tolerate back-pressure on their delicate flow cells, and also is highly disruptive for LS detectors, which are quite difficult to use quantitatively in this way. However, even if the LS and RI detectors are bypassed in the reversed-flow pathway, then the interdetector broadening can become unacceptably large, due in part to the required flow-switching valve between the channel and the detectors, complicating accurate characterization of the analyte. Bypassing the LS and RI detectors also leaves no solvent flowing through them during the relaxation period, requiring yet another pump to keep fluid flowing through them at precisely the same flow rate and pressure to minimize the baseline disturbances which result from the hydraulic changes in the channel. Furthermore, the reversed-flow focussing procedure is known to cause artifactual aggregation of many important analyte species, including proteins, polymers, and liposomes. This results largely from the fact that the two opposing flowstreams tend to concentrate the analyte against the filtration membrane in a relatively small area, leading inevitably to aggregation and other forced interactions. Since one primary use of the flow FFF system is the quantitative characterization of aggregation and association phenomena, often in combination with LS and RI detectors, the reversed-flow focussing procedure is clearly a poor choice.

Another approach to solving the relaxation problem and achieving stopless relaxation is taught by Giddings in U.S. Pat. No. 5,141,651 and described by Giddings in *Sep. Sci. Technol.* 24(9&10), 755 (1989), both of which are incorporated by reference herein. In this method, the channel flow inlet is blocked off or occluded so as to force the incoming sample into a smaller and tighter cross-sectional distribution. When the sample-bearing flow stream encounters the crossflow stream, relaxation occurs by virtue of the existing crossflow field, so that a stop-flow period is not required. Unfortunately, this approach has also not been commercially successful, due to several inherent difficulties. One problem has been the difficulty of fabricating flow FFF devices based on the method taught by this disclosure, in that it calls for a tight seal to be provided by adjacent pieces of spacer material, usually plastic, which have a tendency to leak. Also, the solid (blocked) portion of the upper spacer component tends to bend or buckle under the force of the cross flow, at least changing the cross-sectional area of the membrane if not occluding it completely. Another problem is that reasonable resolution is not always achieved, due partly to the fact that the inlet occlusion takes up a significant fraction, up to one half, of the total channel length and also partly to the fact the channel flow stream must accelerate around the occlusion in the region of the smaller cross-sectional channel area. Yet another difficulty is that this method does not get rid of the so-called "void peaks," which result, in part, from unrelaxed material eluting at the front of the channel flow. Given these deficiencies, it is not difficult to understand why the inlet occlusion approach has not been commercially successful.

It can be seen that each of these existing methods for accomplishing the relaxation of the analyte prior to the flow FFF separation imposes intolerable restrictions and requirements on the fractionation process, including reducing the types and variety of online detectors which can be utilized to characterize the analyte, while increasing the instrumentation complexity and operating costs, decreasing the available resolution, and rendering the respective separation processes cumbersome, inconvenient, and unnecessarily complicated to control. Since the power of flow FFF resides in the use of the correct combination of detectors, often including LS, UV, fluorescence, and RI detectors, the existing relaxation methods and devices are clearly unsuited to the application of flow FFF in many industries, including the biopharmaceutical industry.

If the remaining problem of avoiding these disadvantages of the existing relaxation procedures could be solved, while ensuring complete and efficient stopless relaxation of the incoming analyte sample and also providing a means for calculating the channel width, the flow FFF procedure would become more practical and useful, as well as more routine and automatable, which would in turn permit flow FFF to be applied to the large number of analytical and preparative problems to which it is well suited. It would therefore be highly advantageous to find a promising method for the modification of the flow FFF process to achieve stopless and splitless relaxation without any of the above-noted disadvantages.

SUMMARY OF THE INVENTION

Accordingly, the present invention is directed to an improved flow FFF process without the aforementioned deficiencies which can be implemented on commercially-available high-performance liquid chromatography (HPLC) and low-pressure liquid chromatography (LC) equipment in a manner consistent with the use of sensitive detection technologies.

The improved flow FFF process introduces the analyte into the channel in the channel-inlet flow stream ($V_z$), rather than in a special or dedicated flow stream, and provides an improved flow FFF process which is capable of effecting separations at enhanced rates of speed. The improved flow FFF process maintains the analyte in constant hydrodynamic motion during the separation, in order to avoid particle adsorption to any of the walls or surfaces of the channel. Relaxation is accomplished while avoiding any unnecessary steps which either artifactually concentrate or dilute the analyte. The resulting process avoids the need for stopping or reversing the axial flow during a run, and leads to dramatically-improved compatibility with flow-sensitive detectors such as LS and RI. It also minimizes the number of required pumps—typically only two pumps are needed. Also avoided is the need for a channel-flow switching valve and its controlling software, and a further simplification of the remaining system plumbing, also leading to an increased ease of automation. The improved flow FFF process eliminates void peaks due to incomplete sample introduction or relaxation, and also minimizes artifactual aggregation due to concentration on the filtration membrane, so that a maximal fraction of the entire sample is included in the retained but eluted peaks. The new process and channel width calibration procedure lead to simplified and more accurate calculation of run parameters, including frictional coefficients and diffusion coefficients and their distributions, as well as improved reproducibility of retention times and calculated properties such as distributions of supramolecular masses. These and other properties render the improved flow FFF process capable of being run on commercial HPLC and LC equipment, thereby significantly extending the potential applicability of flow FFF as well as the user base of trained operators. It will be apparent to one skilled in the art that the process of the present invention is applicable to all types of flow FFF channels, including planar and annular, and to all operating modes of flow FFF, including normal, steric, and hyperlayer modes, and to all channel geometries, including parallel-walled, tapered, etc., and to flow FFF separations conducted at any temperature.

The present invention stems from a number of relevant observations. First, most if not all of the peak dispersion which is observed in stop-flow, frit inlet, and inlet splitter experiments appears to result from the way in which the sample is introduced into the channel, so that much of the excessive peak broadening has already occurred by the time that the stop-flow relaxation procedure commences. Since the sample can only undergo further broadening as it relaxes, it would seem preferable to prevent this initial broad dispersion of the analyte band rather than attempting to correct it after it has occurred, and then to minimize any additional dispersion by eliminating the stop-flow procedure. A second observation results from the recognition that the sluggishness of the field-driven transport (i.e. the cross flow rate $V_x$) is only relative—it is only slow because the channel flow $V_z$ is typically fast, The most important and relevant metric is the linear velocity ratio $U_x/U_z$, which is directly proportional to retention. If the channel flow rate $V_z$ is slowed down significantly, then the crossflow linear velocity $U_x$ becomes relatively faster, leading to an increased linear velocity ratio $U_x/U_z$, in which both retention and field-driven relaxation in the cross flow are increased. Another observation is that at lower flow rates much of the momentum imparted to the entering analyte by the high linear velocity in the channel-flow inlet tubing is lost with conventional flow FFF apparatus, which employs inlet tubing of large diameters in order to accommodate the high volumetric flow rates traditionally used in flow FFF experiments.

It has been surprisingly discovered that these shortcomings can be overcome, and the foregoing operating parameters can be manipulated to obtain a new stopless and splitless method of operating a flow FFF channel which offers as good or better resolution as previous flow FFF methods, produces an analyte stream of sufficient concentration and hydraulic quality to enable detection by relevant and appropriate technologies, eliminates much of the equipment and components previously required, and renders the fractionation procedure simple, reliable, rugged, and practical. This set of conditions also avoids artifactual concentration and the need for additional dedicated software, and permit the execution of flow FFF experiments on commercially-available HPLC and LC instruments. The new method will be especially useful in the separation, characterization, and isolation of a wide variety of analytes.

The achievement of stopless and splitless flow FFF relaxation in the present invention results in fractograms which do not exhibit early-eluting system peaks, ensuring that the entire analyte sample is represented in the subsequent calculations. However, the absence of a void peak means that some other means must be found for calculating the channel width w. A useful starting point is the relationship between the retention time $t_r$ and the various experimental parameters for normal-mode flow FFF elution (M.-K. Liu et al., *Prot. Sci.* 2, 1520 (1993)), $$t_r = \frac{\pi \cdot \eta \cdot w^2 \cdot d_h \cdot V_x}{2 \cdot kT \cdot V_z}. \tag{1}$$

where $\eta$ is the viscosity, in poises, $$\eta = \frac{g}{cm \cdot s}, \tag{2}$$

$d_h$ is the hydrodynamic (or Stokes) diameter, k is Boltzmann's constant, $$k = 1.38054 \times 10^{-16} \frac{g \cdot cm^2}{s^2 \cdot K},$$

T is the absolute temperature in K, and $V_z$ and $V_x$ are the volumetric channel and cross-flow rates, respectively, in mL/min. This equation shows the direct dependence of the retention time on the hydrodynamic diameter $d_h$, the channel width w, and the flux ratio $V_x/V_z$. Rearrangement of this equation yields the channel width w in terms of the difference in retention times ($t_2-t_1$) and the difference in hydrodynamic diameters ($d_2-d_1$) of two calibrant analytes, $$w = \sqrt{\left(\frac{t_2 - t_1}{d_2 - d_1}\right) \cdot \left(\frac{2 \cdot k \cdot T}{\pi \cdot \eta}\right) \cdot \left(\frac{V_z}{V_x}\right)}. \tag{3}$$

where $t_1$ and $t_2$ are the measured retention times, in minutes, and $d_1$ and $d_2$ are the respective calibrating analytes' hydrodynamic diameters, in cm.

The dependence of the retention time $t_r$ on the diffusion coefficient D can be made explicit by substituting the Stokes-Einstein equation, $$D = \frac{kT}{3 \cdot \pi \cdot \eta \cdot d_h}, \tag{4}$$

into Equation 1 for the hydrodynamic diameter-based retention time $t_0$ yield an expression for the normal-mode flow FFF retention time $t_r$ for well-retained components, $$t_r = \frac{w^2 \cdot V_x}{6D \cdot V_z}. \tag{5}$$

Rearrangement of this equation yields the channel width w in terms of the difference in retention times ($t_2-t_1$) and the difference in diffusion coefficients ($D_2-D_1$) of two calibrant analytes, $$w = \sqrt{\left(\frac{6 \cdot (t_2 - t_1) \cdot (D_2 - D_1) \cdot V_z}{V_x}\right)} \tag{6}$$

where $t_1$ and $t_2$ are the measured retention times, in minutes, and $D_1$ and $D_2$ are the respective calibrating analytes' hydrodynamic diameters, in cm.

Another component of the present invention is the calculation of the channel width w by the use of one of these two equations or their equivalents. From the channel width w determined in this way can then be calculated the channel void time $t_0$ and the void volume $V_0$, as well as the numerous other parameters useful in the characterization of the analyte mentioned above, such as the distribution of diffusion coefficients or frictional coefficients, and in the characterization of the separation, such as measures of the efficiency such as the height equivalent to a theoretical plate, the resolution, the fractionating power, and the selectivity. Thus, the improved channel calibration procedure of the present invention complements the process improvements which comprise the remainder of the present invention by facilitating the calculation of the channel width w without requiring a discrete void peak in the fractogram.

The present invention comprises an improvement in the flow FFF process for the separation of particles, wherein a carrier fluid containing the particles to be separated is forced through a thin flow channel having one or more inlets and one or more outlets and a field or gradient caused by an orthogonal flow of fluid is used to induce a driving force acting across the thin dimension of the channel perpendicular to the flow axis. The apparatus for use in effecting the above-noted new process can be any conventional flow FFF channel, as described previously, and typically comprises an elongated flow channel enclosed by wall elements, a means for driving a fluid through the channel perpendicular to the long axis of the channel, an inlet means for introducing fluid into one end of the enclosed channel, an outlet means for withdrawing fluid from the other end of the channel, and adjustable flow control means for controlling the fluid flow rates being introduced or withdrawn from the channel.

The improvement of the present invention consists of 1) employing a channel spacer of a minimal thickness (preferably 762 μm (0.030") or less) to minimize the axial dispersion of the entering analyte sample and to maximize the high-velocity component of the relaxation process, and of 2) employing a sufficiently high crossflow rate $V_x$ to aid in rapidly relaxing the entering analyte sample and to maximize the linear crossflow velocity ratio $U_x/U_z$ while avoiding artifactual adhesion of the analyte to the ultrafiltration membrane, and of 3) employing as the accumulation wall an ultrafiltration membrane which is sufficiently tight-pored (preferably 1,000 kDa or less) to provide enough pressure in the channel to maintain a constant cross-sectional area throughout the axial length of the channel while also being of a size which avoids absorption of the analyte to the ultrafiltration membrane, and of 4) employing a sufficiently small channel flow rate $V_z$ so as to minimize the linear channel flow velocity $U_z$ to ensure the rapid and efficient relaxation of the incoming analyte sample against the ultrafiltration membrane and to maximize the linear crossflow velocity ratio $U_x/U_z$ while maintaining a sufficiently large linear channel flow velocity $U_z$ to ensure the presence of a Poiseuille flow velocity distribution within the channel sufficient to effect a flow FFF separation, and of 5) introducing the analyte sample in the single channel flow stream, rather than in a separate or dedicated substream, and of 6) introducing the analyte sample in a minimal volume of fluid, preferably less than about 50 μL, and of 7) continuing both the channel flow and the crossflow streams uninterrupted after the introduction of the sample into the channel, and not introducing any additional substreams into the channel for the purpose of hydrodynamically relaxing the sample, and of 8) calculating the channel width w using either the formula:

$$w = \sqrt{\left(\frac{t_2 - t_1}{d_2 - d_1}\right) \cdot \left(\frac{2 \cdot k \cdot T}{\pi \cdot \eta}\right) \cdot \left(\frac{V_z}{V_x}\right)} \tag{3}$$

or an equivalent expression for the diameter-based width or the formula $$w = \sqrt{\left(\frac{6 \cdot (t_2 - t_1) \cdot (D_2 - D_1) \cdot V_z}{V_x}\right)} \tag{6}$$

or an equivalent expression for the diffusion coefficient-based width, with the variables defined as shown below. Thus, the improvement of the present invention consists of the selection of a combination of eight specific experimental parameters which permit for the first time a simple and efficient technique for relaxing an analyte prior to a flow FFF separation without stopping or reversing the channel flow and without the need for additional flow substreams or complicated and expensive hardware or additional pumps. The present invention is expected to be applicable to all forms of flow FFF, including symmetrical and asymmetrical flow FFF conducted in normal, steric, and hyperlayer modes of operation in both planar and annular flow FFF.

DETAILED DESCRIPTION OF THE INVENTION

Figure 1:
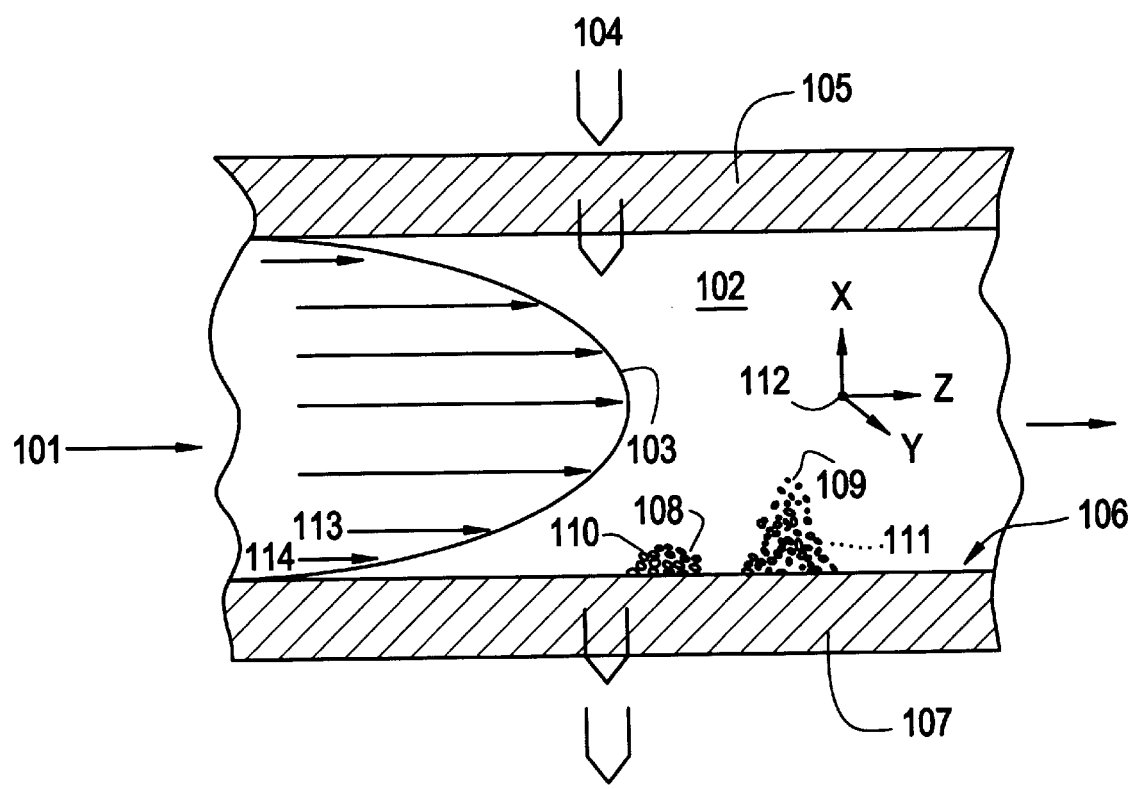
FIG. 1 is an illustration of the essential forces acting to produce flow FFF separation.

The following definitions will be used throughout this disclosure.

Accumulation wall: in FFF generally, the wall towards which sample particles are driven by the applied field; in flow FFF, wherein the field is provided by an orthogonal (crossflow) fluid stream, the accumulation wall is normally composed of a filtration membrane supported by a porous frit.

Analyte: any sample species which can be retained and separated by flow FFF methods, including but not limited to both rigid and deformable particles ranging in size from sub-nanometer to thousands of microns, biological or synthetic polymers and macromolecules, biomolecules, environmental particles, minerals, industrial powders, crystallization products, deoxyribonucleic acid, ribonucleic acid, and other nucleic acids and nucleic acid analogs, unilamellar or multilamellar vesicles or liposomes, micelles, emulsions, proteins, carbohydrates, and lipids, organelles, latices, cells, or any combination of these species, whether or not covalent, of any of these species, whether naturally occurring or man-made.

Analyte sample: the portion of the analyte which is being fractionated.

Asymmetrical flow FFF: a form of flow FFF in which the upper cross-flow inlet frit is replaced by a non-porous solid material, requiring that the channel flow and cross flow enter the channel as a single combined flowstream but permitting separate channel flow and crossflow outlets.

Carrier: the fluid employed in flow FFF or chromatography to contain the dissolved or suspended analyte during the separation process.

Channel flow: symbolized herein as $V_z$, the fluid flow which enters at the channel flow inlet at one tip of the channel, passes through the channel over the surface of the filtration membrane and parallel to it, and exits from the channel flow outlet end of the channel at the other tip; in the present invention, this flow stream is also the sample inlet stream.

Channel form: the physical format of the channel, such as planar or annular.

Channel spacer geometry: the shape of the portion cut out from the channel spacer to form the fractionation channel.

cm: centimeter, one hundredth of a meter.

Cross flow: symbolized herein as $V_x$, in symmetrical flow FFF the fluid flow which enters the channel through the crossflow inlet frit perpendicular to the channel flow, traverses the channel and mixes with the fluid therein, and exits the channel through the filtration membrane and the crossflow outlet frit perpendicular to the channel flow; in asymmetrical flow FFF the fraction of the fluid flow which enters the channel along with the channel flow through the channel flow inlet frit, traverses some or all of the channel length and exits the channel through the filtration membrane and the crossflow outlet frit perpendicular to the channel flow.

Depletion wall: in FFF generally, the wall opposite the accumulation wall, from which particles are driven away by application of the applied field; in flow FFF, wherein the field is provided by an orthogonal (crossflow) fluid stream, the depletion wall is normally composed of a porous inlet frit.

FFF: field-flow fractionation; a family of techniques in which retention of an analyte in a thin, open channel is accomplished by the application of a field essentially perpendicular to the flow of the analyte (the $V_z$ flow) along the long axis of the channel.

Field: a force which, when applied to an FFF channel, has the effect of displacing the analyte away from the depletion wall and towards the accumulation wall, in a direction perpendicular to the axial flow, thus causing FFF retention.

Flow FFF: the subtechnique of field-flow fractionation in which the driving force or field leading to retention of the analyte is provided by a crossflow of fluid $V_x$ essentially perpendicular to the channel flow ($V_z$) axis, and which can be conducted at any temperature, whether it be at or near the ambient temperature, at a temperature below the ambient temperature, or at a temperature above the ambient temperature, and whether or not the temperature is controlled during the fractionation experiment.

Flux ratio: symbolized herein as $V_x/V_z$, the ratio of the volumetric cross flow rate $V_x$ to the volumetric channel flow rate $V_z$.

Fractionation: the achievement of some degree of separation, not necessarily complete, of components of a mixture from one another based upon some difference in their chemical or physical properties.

Frit: a piece of solid but porous material through which a fluid can flow.

Frit inlet substream: in channels so equipped, a substream of the channel flow consisting of fluid entering the channel through a separate frit section near the inlet end.

Frit outlet substream: in channels so equipped, a substream of the channel flow consisting of fluid exiting the channel through a separate frit section near the outlet end.

HPLC: high-performance liquid chromatography.

LC: liquid chromatography.

$\mu$m: micrometer, one millionth of a meter.

Mobile phase: the fluid employed in chromatography or flow FFF to contain the dissolved or suspended analyte during the separation process.

nm: nanometer, one billionth of a meter.

Particle: same as analyte, typically used to refer to a species as a point object without reference to its specific properties, such as size or shape.

Poiseuille flow: the distribution, typically parabolic, of flowstream velocities characteristic of smooth, laminar flow in narrow passages.

Sample inlet stream: the stream of fluid which brings the dissolved or suspended sample into the channel; in the present invention, this flow stream is identical to the channel flow inlet stream and enters at the inlet tip of the channel.

Sample outlet stream: the stream of fluid carrying the sample material out of the channel, from the outlet tip of the channel, normally flowing into a detector; in the present invention, this flow stream is also the channel flow outlet stream.

$U_x$: the linear crossflow velocity at the filtration membrane surface, often expressed in $\mu$m/sec.

$U_z$: the linear channel flow velocity through the channel's cross sectional area, often expressed in $\mu$m/sec.

Velocity ratio: symbolized herein as $U_x/U_z$, the ratio of the linear crossflow velocity $U_x$ to the linear channel flow velocity $U_z$.

Void time: the time required for one channel volume of the channel flow to pass through the channel.

Void volume: the volume, usually expressed in mL, enclosed by an object; for a flow FFF channel, it is the volume between the crossflow inlet frit and the filtration membrane and along the entire length and breadth of the channel; for other components, such as pieces of capillary tubing, it is the geometric volume of the swept inner diameter of the component.

$V_x$: the volumetric crossflow rate, typically expressed in mL/min, which is independent of the configuration of the channel or spacer.

$V_z$: the volumetric channel flow rate, typically expressed in mL/min, which is independent of the configuration of the channel or spacer.

Wall: any and all types of wall elements, such as accumulation walls and depletion walls, enclosing the thin flow FFF channel, including straight wall elements and curved wall elements as would be found in a cylinder-shaped channel.

The present invention comprises an improvement to the process of flow field-flow fractionation, the practice of which will become more clear by reference to the accompanying figures.

FIG. 1 is a schematic representation of the forces and components which produce a separation in flow FFF. The fluid 101 comprising the channel flow ($V_z$) passes axially through the thin passage of the channel 102, forming a parabolic Poiseuille flow velocity distribution 103. Fluid 104 comprises the crossflow stream $V_x$, which passes through the crossflow inlet frit 105 and the channel space 102 cut out from the channel spacer material before penetrating the filtration membrane 106 and exiting through the crossflow outlet frit 107. Under the influence of the crossflow fluid 104, a large analyte species 108 and a small analyte species 109 are driven to their equilibrium positions against the filtration membrane 106. The large species 108 hovers over the filtration membrane as a cloud of particles with a small average distance 110 from the membrane, while the small species 109 hovers over the filtration membrane as a cloud of particles with a larger average distance 111 from the membrane. A set of orienting axes 112 can be used to identify the various dimensions of the channel, with the width referred to as 'x', the breadth referred to as 'y', and the axial dimension referred to as 'z'. On average, the smaller particles 109 will be driven by fluid 101 at an average velocity 113, and will therefore elute from the channel earlier than the larger particles 108, which will be driven by fluid 101 at an average velocity 114.

The channel flow fluid 101 and the crossflow fluid 104 in FIG. 1 can be any liquid, gas, plasma, or supercritical fluid containing any or no additional solid, liquid, gaseous, or other components. Fluids 101 and 104 can be, but need not be, identical to each other. Most commonly, fluid 101 comprises either water or an organic solvent containing dissolved modifying agents. In the preferred embodiment, fluid 101 consists of an aqueous solution of sodium chloride and a buffer, such as 150 mM NaCl, 10 mM sodium phosphate, and 200 parts per million (ppm) of sodium azide at a pH of 7.40.

Figure 2:
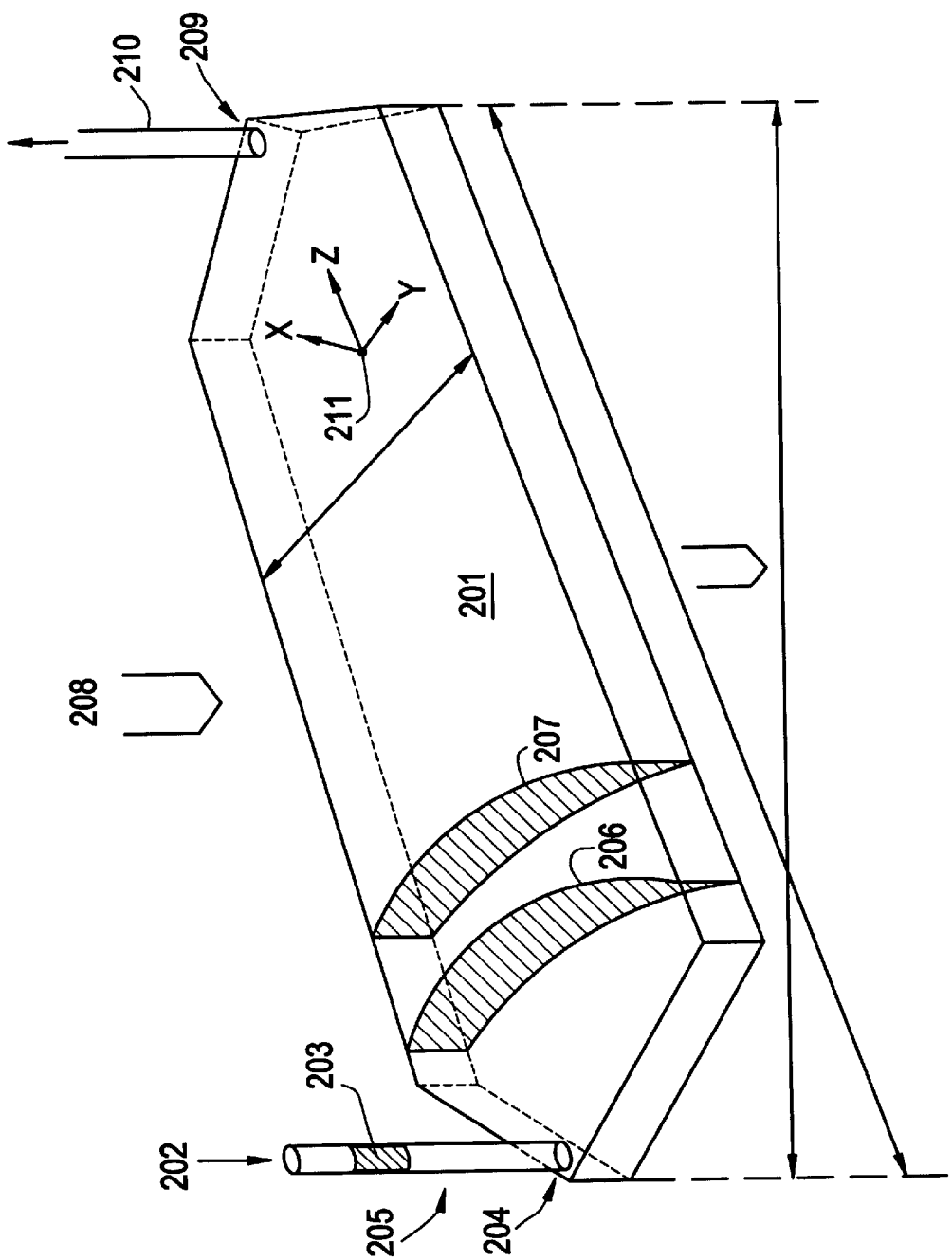
FIG. 2 is a schematic diagram of separation in a flow FFF channel.

The flow FFF process of the present invention is conducted in a thin ribbon-like passage called a channel, in which two orthogonal fluid flows intersect and intermingle. FIG. 2 presents a schematic illustration of such a flow FFF channel. The channel 201 is typically 2.0 cm broad, 28.5 cm long at the tips, and 0.127 mm wide, although the length, breadth, and shape can vary significantly from those given. The fluid 202 comprising the channel flow $V_z$ and bearing the analyte sample 203 enters channel 201 from the $V_z$ inlet port 204, which consists of a length of capillary tubing 205 with an inside diameter ranging from 762 $\mu$m (0.030") down to as small as can be manufactured, but more typically ranges between 254 $\mu$m (0.010") and 76 $\mu$m (0.003"). The incoming fluid 202 deposits sample 203 into channel 201, where the components of sample 203 separate into the two curved bands 206 and 207 as they migrate down the channel under the influence of the crossflow 208. Real samples may contain any number of separable components, from none or a single one to hundreds or more. At the far end of the channel, the sample bands 206 and 207 exit the channel through the $V_z$ outlet port 209, which consists of a piece of capillary tubing 210 which need not be of the same material or dimensions as the $V_z$ inlet port 204 or capillary tubing 205. As in FIG. 1, a set of orienting axes 211 can be used to identify the various dimensions of the channel, with the width referred to as 'x', the breadth referred to as 'y', and the axis referred to as 'z'. The sample 203 can be any analyte, as defined above to include essentially any species which can be dissolved or suspended in the fluid 202 and can be retained by the filtration membrane 106 in FIG. 1, but more commonly consists of proteins, polymers, nucleic acids, macromolecules, vesicles, and similar particles. In the preferred embodiment, sample 203 consists of proteins such as lysozyme, cytochrome, albumin, immunoglobins, pharmaceutical proteins, macromolecules such as polymers and nucleic acids, pharmaceutical particles such as protein-polymer conjugates or coated microspheres, or aqueous vesicles such as liposomes or micelles.

Figure 3:
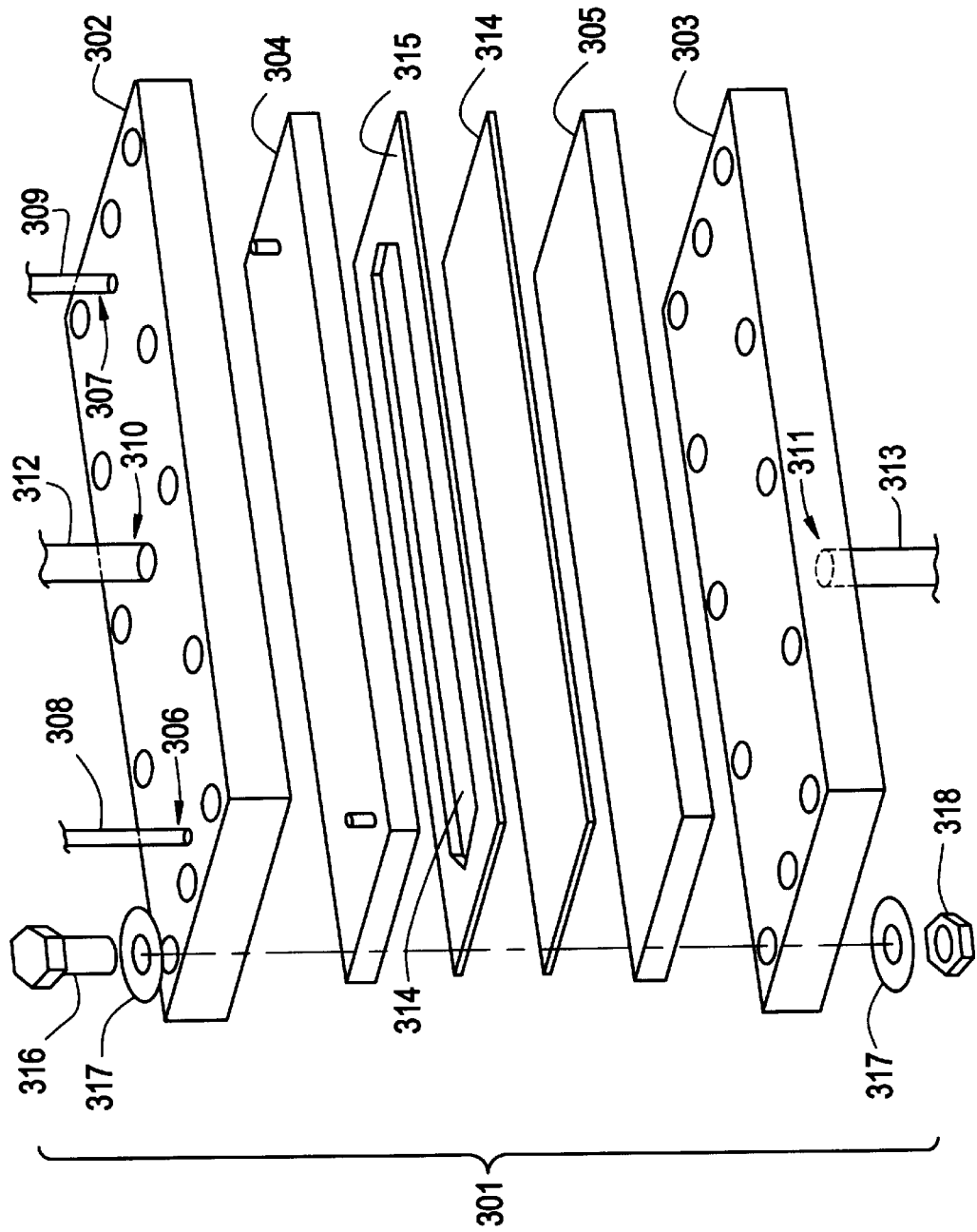
FIG. 3 is an exploded view of a typical flow FFF channel.

FIG. 3 schematically illustrates the type of flow FFF channel which can be utilized in the practice of the present invention. The channel device 301 consists of an upper housing block 302 and a lower housing block 303 into which the porous inlet frit 304 and outlet frit 305 are sealed by any convenient means, including pressing, molding, or bolting into place, or sealing into place with silicone elastomer, caulking, or epoxy or any other type of adhesive or glue. The housing blocks 302 and 303 can be made of any material which can withstand the fluids which are used in the improved flow FFF process, and need not be fabricated from the same or even similar materials as each other. Most commonly, the housing blocks 302 and 303 are machined from stainless steel or plastics such as poly (methylmethylacrylate), although they can in principle be made of other materials such as titanium or plastics such as poly(propylene), or poly(etheretherketone) (PEEK). In the preferred embodiment, the housing blocks 302 and 303 are machined from poly(methylmethylacrylate), stainless steel, or titanium castings, and the various port holes are drilled and machined as needed.

The various holes, ports, and excavations in the housing blocks 302 and 303 in FIG. 3 can be machined into place or cast or molded in place as the housings are produced, but most commonly are machined into blank housing blocks. The holes for the channel flow inlet port 306 and channel flow outlet port 307 are drilled to allow the insertion of pieces of channel flow inlet tubing 308 and channel flow outlet tubing 309. Tubing 308 and 309 can be made of any material compatible with the fluid being used in the improved flow FFF process, and can be made with any outer or inner diameter. Typically, it is desirable to minimize the diameter and the volume of these pieces of tubing consistent with the pressure and operational limits of the apparatus. Similarly, the holes for the crossflow inlet port 310 and crossflow outlet port 311 are drilled to allow the insertion of pieces of crossflow inlet tubing 312 and crossflow outlet tubing 313. These pieces of tubing 312 and 313 can also be made of any material compatible with the fluid being used in the flow FFF process, and can also be made with any outer or inner diameter. The inlet tubing 308 or 312 and the outlet tubing 309 or 313 can be made from the same or different materials, or possess the same or different outer or inner diameters. Most commonly, the tubing pieces 308 and 309 are made from poly(tetrafluoroethylene), stainless steel, or poly(etheretherketone), with an outer diameter of $\frac{1}{16}$" and an inner diameter ranging from 25 $\mu$m (0.001") to 762 $\mu$m (0.030"). In the preferred embodiment the channel flow inlet tubing 308 consists of a short length of $\frac{1}{16}$" O.D. poly (etheretherketone) tubing with an I.D. of 254 $\mu$m (0.010"), and the channel flow outlet tubing 309 consists of a longer length of $\frac{1}{16}$" O.D. poly(etheretherketone) tubing with an I.D. of 127 $\mu$m (0.005"), while the crossflow inlet tubing 312 consists of a short length of $\frac{1}{16}$" O.D. poly (tetrafluoroethylene) tubing with an I.D. of 762 $\mu$m (0.030"), and the crossflow outlet tubing 313 consists of another length of $\frac{1}{16}$" O.D. poly(etheretherketone) tubing with an I.D. of 762 $\mu$m (0.030").

The frits 304 and 305 in FIG. 3 can be manufactured from any materials which can withstand, but are permeable to, the fluids which are used in the improved flow FFF process. They need not be fabricated from the same or even similar materials as each other. The frits 304 and 305 are most commonly made from finely-divided ceramic, metal, or plastic sintered to an average pore size varying from about 0.1 $\mu$m to 100 $\mu$m. The most useful frit materials include aluminum oxide ceramics, titanium, and plastics such as poly(ethylene), poly(propylene), and poly (etheretherketone). In the preferred embodiment, frits 304 and 305 are made from porous sintered ceramic with a mean pore size of 5 $\mu$m, such as is available from Ferro Corporation in Cleveland, Ohio.

Sandwiched between the housing blocks 302 and 303 in FIG. 3, and resting immediately on top of the outlet frit 305, is a filtration membrane 314, typically an ultrafiltration membrane. The membrane must be permeable to the fluid used as the carrier in the flow FFF experiment, but must not dissolve in it or be disrupted by it, and it must also retain the analyte of interest and possess an asymmetrical structure in order to act as a surface filter rather than as a depth filter. Such filtration membranes can be purchased from a number of commercial suppliers, such as Pall-Filtron in Northborough, Mass., and Millipore of Bedford, Mass., both of whom offer membranes made from many different materials and with a broad range of pore sizes ranging from about 500 Da up to several microns. Most commonly, commercial ultrafiltration membranes made from regenerated cellulose, poly(ethersulfone), or poly(sulfone) in pore sizes from 1 kDa up to 10 kDa are employed. In the preferred embodiment, a 3 kDa membrane made from regenerated cellulose is used with an aqueous PBS carrier fluid.

Flow FFF separations benefit from constant $V_z$ and $V_x$ flow rates, both spatially and temporally. Flow rate fluctuations in time create hydraulic disturbances which negatively impact the resolution of the experiment. Similarly, flow rate disturbances can occur spatially, as when a filtration membrane protrudes further into the channel space at one location than it does in another. Because of the resulting variations in the cross-sectional area of the channel, the channel flow stream $V_z$ will experience acceleration and deceleration during its travel axially down the channel. This, in turn, creates regions of varying velocity ratio $U_x/U_z$, which act to increase the dispersion of the sample and attenuate the efficiency and resolution. Thus, the use of tighter-pored membranes is helpful both to retain small analytes such as proteins, polymers, and liposomes, and also to provide sufficient backpressure within the channel to "inflate" the membrane out to its physical boundaries (e.g. the crossflow outlet frit), thereby preventing expansion of the membrane into the channel at any point and ensuring a consistent cross-sectional area axially along the channel's length.

Located immediately above the filtration membrane 314 in FIG. 3 is a channel spacer 315, which is sandwiched between the filtration membrane 314 and the combined housing block 302 and inlet frit 304. Into the channel spacer 315 is cut a hole 319 which determines the shape of the channel. The channel spacer 315 can be made from any material which can withstand the fluids which are used in the improved flow FFF process, and which is commercially available in thin sheets with consistent thickness, and which also possesses sufficient dimensional stability to maintain the size and shape of the channel. Typically, a spacer material is chosen with which the analyte does not interact and to which it does not bind. Such materials can include a wide variety of plastics, metals such as aluminum or stainless steel, ceramics, or glasses, but the channel spacer is most commonly cut from a sheet of Mylar or poly(ester), with a thickness ranging from 76 $\mu$m (0.003") to 762 $\mu$m (0.030"). In the preferred embodiment, the channel spacer is cut from a sheet of 127 $\mu$m (0.005") Mylar.

The entire flow FFF channel assembly 301 in FIG. 3 is held together by a series of bolts 316 to which are affixed washers 317 and nuts 318 and tightened to a modest torque of 5–100 inch-pounds each. Enough bolts 316 are located around the edges of the housing blocks 302 and 303 to ensure that the pressure exerted by the bolts is evenly distributed across the surface of the channel spacer 315 and the filtration membrane 314, ensuring a uniform cross-sectional shape along the entire axial length of the channel. Channels with housing blocks 302 and 303 which are constructed of harder materials, such as stainless steel, require fewer bolts 316, washers 317, and nuts 318, which in turn renders the changing of the membrane 314 and channel spacer 315 faster and simpler. In the preferred embodiment, a total of 18 bolts are used to fasten the components together.

For the practice of the present invention in conjunction with asymmetric flow FFF, several modifications to the channel 301 would be required. First, the inlet crossflow frit 304 would either be replaced by a piece of solid, non-porous material 304 which would fit into the channel housing 302 and seal the channel assembly 301 from leaks, or the inlet crossflow frit 304 would be eliminated by using an upper channel housing 302 which incorporates the shape and position of the inlet crossflow frit 304. Because the crossflow inlet frit 304 would become non-porous, the crossflow inlet 310 and its associated tubing 212 would be eliminated, and the crossflow would be pumped along with the channel flow into the channel through the channel flow inlet 306 via its associated tubing 308. In addition, the channel spacer 315 would typically be replaced with a tapered channel spacer such as spacers 406, 411, or 416 in FIG. 4. The relative volumetric channel outlet and crossflow outlet flows would be adjusted by the selection of appropriately constrictive tubing 309 and 313, or by the use of alternative flow regulators or constrictors.

Although the flow FFF channel depicted in FIG. 3 illustrates a planar example of the flow FFF process, it will be apparent to one skilled in the art that process of the present invention can easily be practiced in a flow FFF channel of cylindrical cross section. Such a cylindrical flow FFF channel can possess either inside and outside porous frits, rendering the process symmetrical, or only an outside or an inside porous frit, rendering the process asymmetrical.

Figure 4:
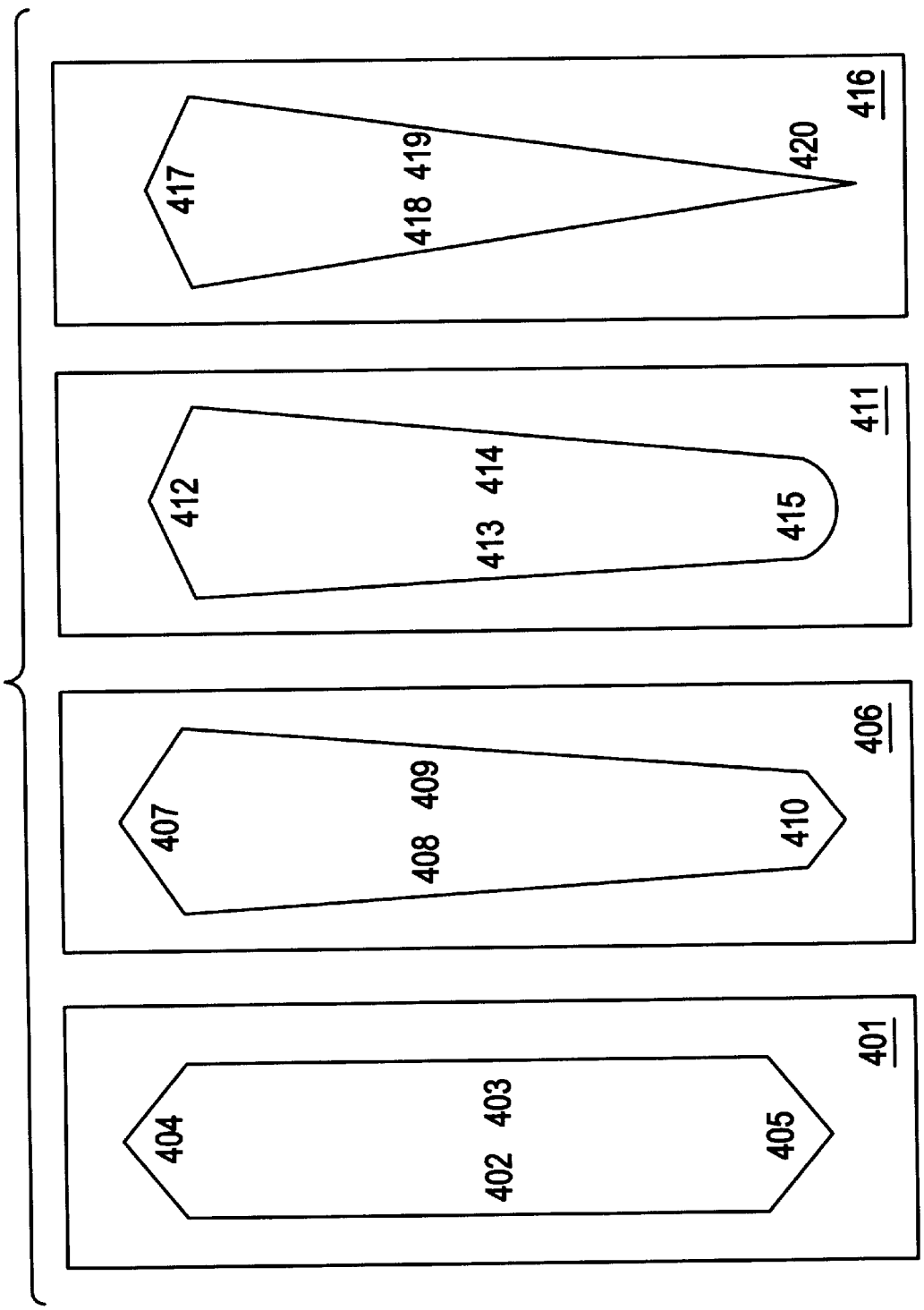
FIG. 4 presents four typical channel spacers of varying geometry.

The geometry of the channel is determined by the shape of the hole which is cut out from the center of the channel spacer 315 in FIG. 3. Although in principle almost any shape can be cut from the channel spacer to form the channel, FIG. 4 illustrates four especially useful channel geometries. Channel spacer 401 consists of parallel edges 402 and 403, with triangular or nearly triangular endpieces 404 at the channel flow inlet and 405 at the channel flow outlet, which triangular endpieces may or may not be identical in size and shape to each other. Channel spacer 406 consists of a triangular channel flow inlet endpiece 407 and edges 408 and 409 which are tapered towards each other as they approach the smaller triangular endpiece 410 at the channel flow outlet. Channel spacer 411 consists of a triangular channel flow inlet endpiece 412 and edges 413 and 414 which are tapered towards a curved channel flow outlet endpiece 415, which is smaller than the inlet endpiece 412. Channel spacer 416 consists of a triangular channel flow inlet endpiece and edges 418 and 419 which taper to a point as they approach the channel flow outlet port 420. In the preferred embodiment, a hole similar to that in channel spacer 401 and with a tip length of 28.5 cm is cut from a 0.127 $\mu$m (0.005") Mylar sheet to form the channel spacer.

Figure 5:
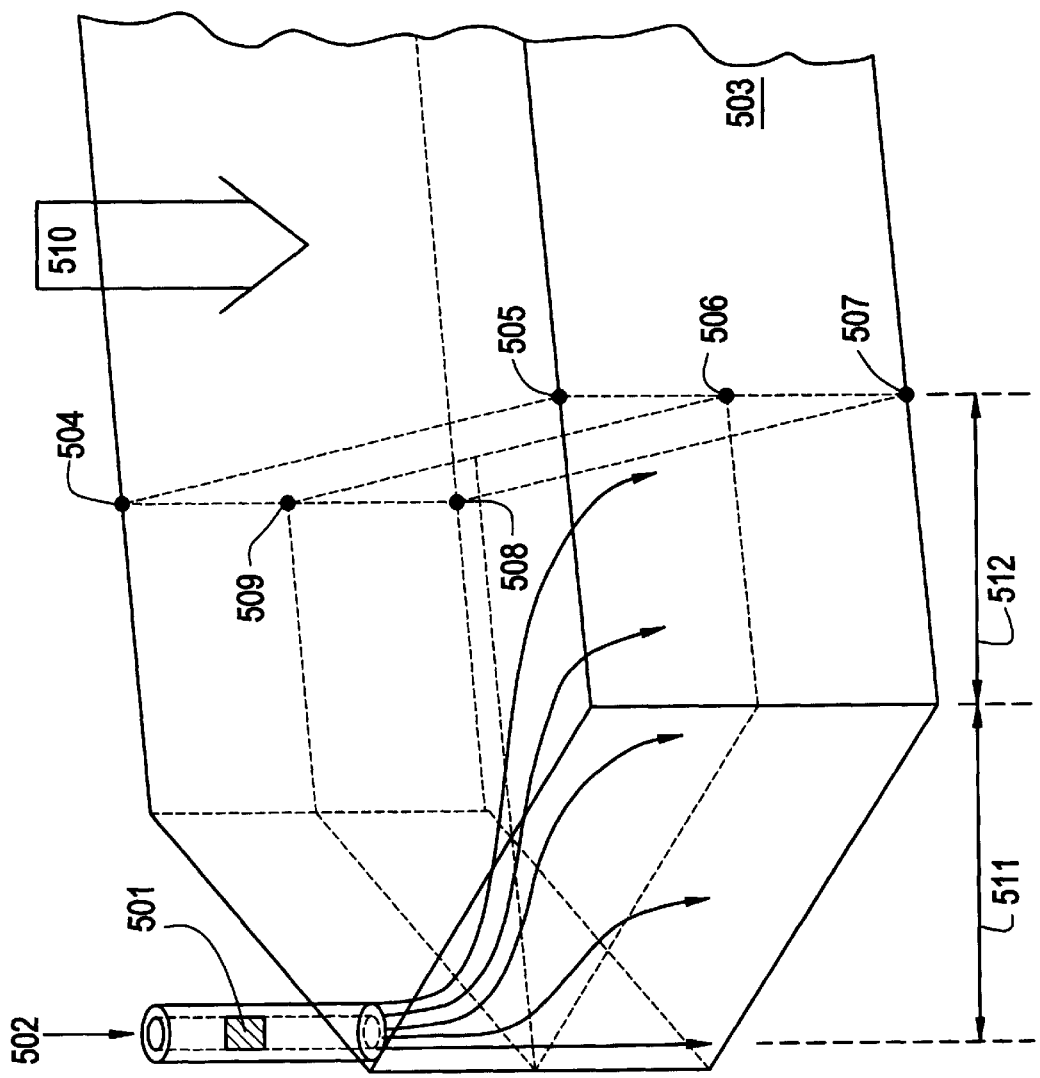
FIG. 5 is a schematic view illustrating the dispersion of an analyte sample band as it enters a flow FFF channel.

FIG. 5 illustrates the dispersion of an analyte sample band 501 in the channel flow carrier fluid 502 as it enters a channel 503 of width 504–508 and breadth 504–505 under the influence of a cross flow 510. The rectangle defined by points 504–505–507–508 is the cross-sectional area of the channel at the point where the analyte sample 501 penetrates furthest into the channel before it is completely relaxed by the crossflow 510. Due to the width 504–508 of the channel, the entering analyte band 501 penetrates the channel to a distance (511+512) before it is fully relaxed by the cross flow 510.

On the other hand, if the channel width in FIG. 5 were half the previous value, i.e. its cross-sectional area was only 504–509, and the channel flow rate $V_z$ were reduced proportionately to the reduction in the cross-sectional area 504-505-506-509 such that the linear velocity of the carrier fluid 502 remained constant, then the entering sample 501 would be swept only a fraction of the former distance (511+512), or roughly a distance 511, before being fully relaxed by the cross flow 510. Thus, minimizing the width of the channel by minimizing the thickness of the channel spacer improves the fractionation process both by reducing the dispersion of the entering analyte sample and by increasing the concentration of the resultant analyte sample bands. In addition, the thinner channel increases the contribution to the relaxation efficiency from the high-velocity channel flow inlet stream 502. The thickness 504–509 of the channel spacer is therefore chosen to be the minimum thickness possible commensurate with the expected height of the cloud of analyte particles above the filtration membrane.

Additional insight into the efficiency of the flow FFF experiment is available from a detailed comparison of the stop-flow and the stopless and splitless flow FFF experiment. A symmetrical, parallel-walled channel with a 254 $\mu$m (0.010") Mylar spacer and a tip-to-tip length of 28.5 cm has a nominal surface area of 53.5 cm$^2$. Under conditions of sufficient channel pressure, this channel exhibits a width of approximately 220 $\mu$m, and therefore a cross-sectional area of 0.0440 cm$^2$ and a geometrical channel volume of 1.177 mL, so that the linear channel flow velocity $U_z$ in the central portion of the channel (i.e. where the channel breadth is 2.0 cm) is 1,840 $\mu$m/sec. Under operating conditions typical for a protein fractionation in the stop-flow mode, with $V_z$=0.485 mL/min and $V_x$=3.44 mL/min, the linear velocity $U_x$ of the cross flow stream as it passes through the filtration membrane is 10.7 $\mu$m/sec. Channel inlet tubing of 508 $\mu$m (0.020") I.D. is typical of commercial flow FFF channels, so that the linear velocity $U_z$ of the incoming channel flow stream at the top of the channel at a $V_z$ of 0.485 mL/min is 39,900 $\mu$m/sec (i.e. 39.9 mm/sec). Thus, during the fractionation experiment the analyte sample travels through the $V_z$ inlet tubing at 39,900 $\mu$m/sec into the channel, whereupon it becomes exposed to the 10.7 $\mu$m/sec crossflow field resulting from the relatively weak volumetric flux ratio $V_x/V_z$ of 7.09 and a linear velocity ratio $U_x/U_z$ of 5.825×10$^{-3}$. Immediately upon entrance to the channel, the analyte sample begins a linear deceleration over several seconds to a linear velocity $U_z$ of 1,840 $\mu$m/sec which is maintained through the remainder of the parallel-walled portion of the channel. Finally, the channel flow begins a linear acceleration from 1,840 $\mu$m/sec back up to 39,900 $\mu$m/sec over several seconds and exits the channel through the 508-$\mu$m (0.020") $V_z$ outlet tubing.

The same symmetrical, parallel-walled flow FFF channel as considered above can be configured and operated according to the stopless and splitless procedure of the present invention. The channel is fitted with a 127-$\mu$m (0.005") Mylar spacer but still has a nominal surface area of 53.5 cm$^2$. With sufficient channel pressure, this channel exhibits a width of approximately 95 $\mu$m, for a geometrical channel volume of 0.508 mL, or 508 $\mu$L, and a cross-sectional area of 0.0190 cm$^2$, or 43% less than the 220-$\mu$m channel formed from the 254-$\mu$m (0.010") spacer as described above. Under operating conditions typical for a protein fractionation in the stopless mode, with $V_z$=0.100 mL/min and $V_x$=3.900 mL/min, the linear velocity $U_x$ of the cross flow stream as it passes through the filtration membrane is 12.17 $\mu$m/sec. The linear channel flow velocity $U_z$ in the central portion of the channel (i.e. past the cross-sectional area where the channel breadth is 2.0 cm) is 877 $\mu$m/sec. Channel inlet tubing of 127 $\mu$m (0.005") I.D. is typically employed for the channel flow inlet, so that the linear velocity $U_z$ of the incoming channel flow stream at 0.100 mL/min is 131,000 $\mu$m/sec (i.e. 131 mm/sec). Thus, during this stopless fractionation experiment the analyte sample travels through the $V_z$ inlet tubing at 131,000 $\mu$m/sec into the channel, whereupon it becomes exposed to the 12.17 $\mu$m/sec crossflow field at a volumetric flux ratio $V_x/V_z$ of 39.0 and a linear velocity ratio $U_x/U_z$ of 13.88×10$^{-3}$ as it begins a linear deceleration over several seconds to a linear velocity $U_z$ of 877 µm/sec through the parallel-walled portion of the channel. Finally, the channel flow begins a linear acceleration over several seconds from 877 µm/sec back up to 131,000 µm/sec and exits the channel in the 127-µm (0.005") $V_z$ outlet tubing.

The gain in overall analytical efficiency and resolution in the stopless technique is seen to result from a large number of modest improvements. For example, in the stop-flow technique, despite the wider 220-µm channel width the channel flow velocity $U_z$ through the main portion of the channel in the stop-flow experiment is 172 time the crossflow velocity $U_x$, a value which seems wastefully high in comparison to the channel flow velocity $U_z$ of 72.1 times the crossflow velocity $U_x$ in the stopless separation. The linear channel flow velocity $U_z$ of 877 µm/sec for the stopless separation is only about half of that employed in the stop-flow method, 1,840 µm/sec, leading to a further improvement in retention. The cross-flow velocity is also about 20% higher, so that the improvement in the linear velocity ratio $U_x/U_z$ resulting from these advantages is 2.4-fold, the same improvement in relaxation efficiency predicted for a 5.5-fold higher stopless volumetric flux ratio with a channel only 43.2% the width. The analyte particles hit the channel inlet with 3.33 times as much momentum as in the stop-flow experiment, but are carried in a $V_z$ stream moving only about half as fast once it enters the channel inlet. Thus, the advantages of the new stopless method appear to result from a combination of the improved relaxation, probably ranging in magnitude from the crossflow limit of about 20% faster to the high-velocity relaxation limit of about 330% faster, and the 240% improvement in retention due to the reduced linear velocity ratio $U_x/U_z$ in the stopless method.

Thus, the cumulative advantage of the various improvements of the present invention is clear. With a crossflow velocity $U_x$ of 12.17 µm/sec in the stopless method, relaxation due to the crossflow stream alone would require 7.81 sec, compared with 20.6 sec for the wider 220-µm channel. However, with the lower channel flow velocity $U_z$ of 877 µm/sec, the sample effectively travels only 6,850 µm down the channel, yielding a tight analyte band on the filtration membrane which covers only 1.37 cm². In contrast, in the stop-flow experiment the analyte sample would have traveled 37,900 µm, or 37.9 mm, during its 20.6-sec relaxation time in the crossflow stream, yielding a large 7.58 cm² band on the filtration membrane. Since the resolution of these bands is proportional to the surface area they occupy, the ratio of these surface areas, 5.53, suggests the significant improvement in the resolving power of the flow FFF experiment resulting from the cumulative improvements of the present invention.

Because the mass of the analyte particles remains constant regardless of their velocity, the momentum of the particles, which is the force which actually delivers the particles to the desired position along the filtration membrane, is proportional to the linear velocity. If the hydraulic slowing of the entering analyte is considered to be independent of the velocity, then the relaxation time is also reduced in proportion to the incoming sample velocity. If it is assumed further that the linear axial channel flow velocity is constant (or at least that it changes linearly for triangular endpieces), then a proportional decrease in the relaxation time will lead to a proportionate reduction in the axial length and overall size of the deposition zone. This quite literally "reduced band width" translates directly to improved resolution.

Directly injecting the minimized channel flow stream at a relatively high linear velocity by minimizing the diameter of the channel flow inlet tubing reduces the relaxation time by some amount, which at its maximum would be the time required to traverse the 95-µm channel width at the entry velocity $U_z$, but usually would be somewhat less owing to some degree of hydraulic attenuation of the velocity accompanying the entry of the analyte sample at a 90° angle into the channel and the deceleration of the channel flow in the triangular inlet endpiece. A channel flow stream entering the channel from 127 µm (0.005") tubing and travelling at a linear velocity $U_z$ of 131,000 µm/sec in a volumetric flow of 0.100 mL/min would traverse the entire channel width in 725 µsec, during which time it would have traveled only 0.636 µm down the channel and covered an area of only $1.27 \times 10^{-4}$ cm². While the precise attenuation of this incoming channel flow velocity is not known, clearly a significant reduction in the channel thickness will reduce this attenuation and increase the extent to which this incoming velocity reduces the relaxation time. This effect of improving the efficiency of relaxation by rapidly injecting the analyte in narrow tubing, and the synergistic advantages of this technique with thinner channels, is not anticipated in the prior art, but is taken advantage of in the present invention.

Of course, it is anticipated that there might exist linear velocities which are too high to permit rapid and efficient relaxation of the analyte against the membrane, either due to turbulence at the higher flow rates or to the analyte particles effectively "bouncing off" the filtration membrane and moving out into the channel. It may therefore be necessary to further optimize the exact conditions of membrane, flow rates, etc., for each analyte type. As a practical matter, however, this may not pose undue difficulty, since the optimization of separation conditions is a frequent and accepted part of separation science.

Figure 6:
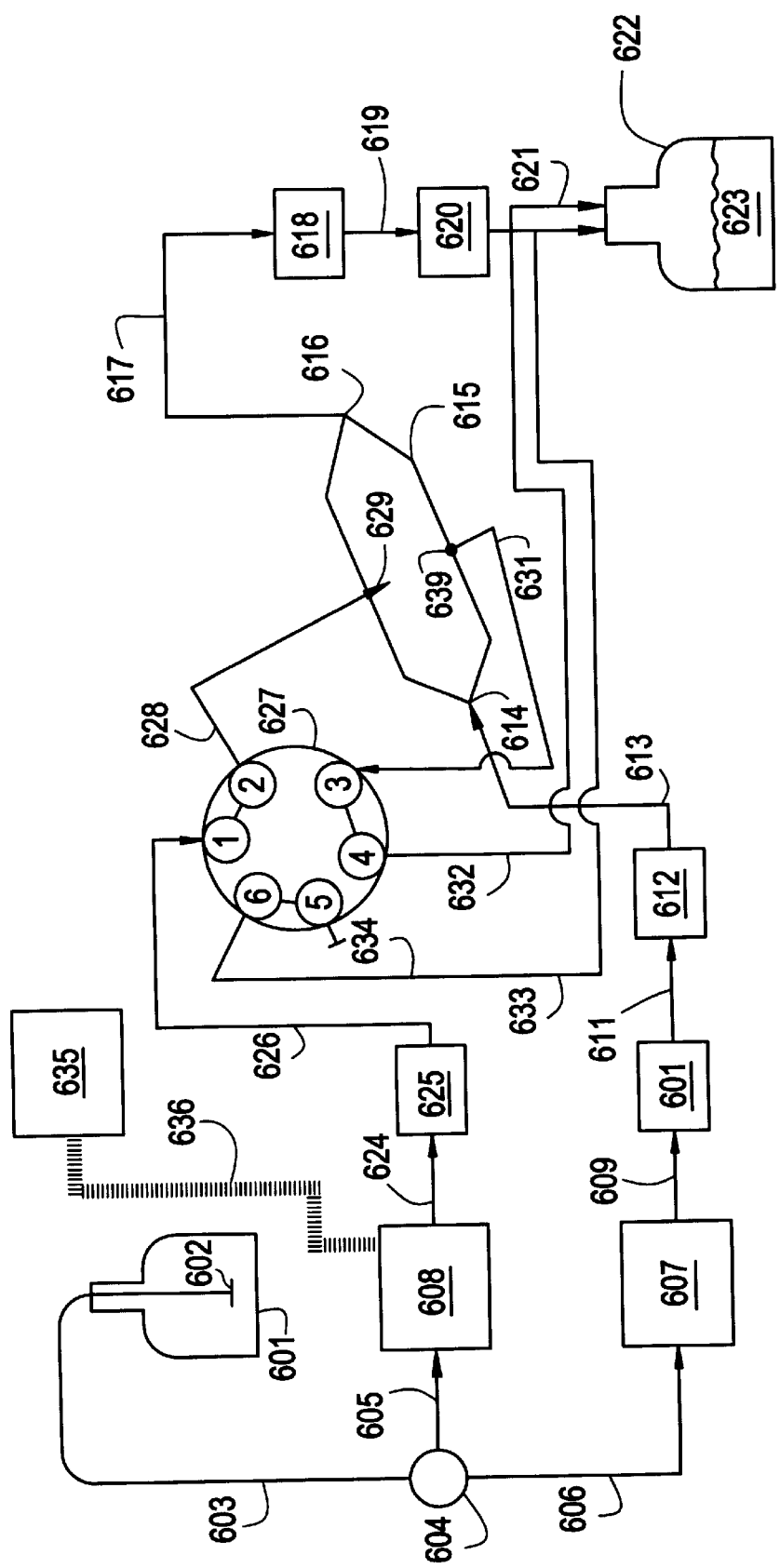
FIG. 6 is a block diagram of the typical components in an HPLC-based stopless and splitless flow FFF system.

It is intended that the present invention be practiced in conjunction with the components of commercially-available, modern HPLC and LC systems, modified for use with flow FFF channels. FIG. 6 illustrates a typical environment in which the present invention will be utilized, showing the arrangement of the various components. Reservoir 601 contains the fluid 602 to be used as the carrier. A piece of poly(tetrafluoroethylene) (FTFE) tubing 603 conducts the carrier fluid 602 to tee 604, from which additional pieces of PTFE tubing 605 and 606 conduct the carrier fluid 602 to channel flow pump 607 and crossflow pump 608, respectively. Capillary tubing 609 conducts the carrier fluid 602 from the $V_z$ pump 607 to the in-line filter 610, and capillary tubing 611 conducts carrier 602 to the autosampler 612. Additional capillary tubing 613 then conducts the carrier 602 bearing the analyte sample to the $V_z$ inlet 614 of the channel 615. Carrier fluid 602 then passes out of the $V_z$ outlet 616 through additional capillary tubing 617 and then passes through the light-scattering detector 618, capillary tubing 619, and one or more additional detectors 620, before passing via capillary tubing 621 to waste bottle 622 containing waste 623.

In the crossflow stream, capillary tubing 624 conducts the crossflow carrier fluid 602 through in-line filter 625 and capillary tubing 626 before entering port 1 of an optional six-port, two-position electrically-actuated flow switching valve 627, in which port S is blocked off by a plug 634. When the six-port switch 627 is in "Run" mode, carrier fluid 602 passes via an internal channel to port 2 of valve 627, from which it is conducted by capillary tubing 628 to the $V_x$ inlet 629 of channel 615. The carrier fluid 602, newly mixed in channel 615 with the incoming channel flow fluid from channel flow inlet 614, passes out of the $V_x$ outlet 630 through additional capillary tubing 631 and then passes into port 3 of valve 627. The crossflow passes from port 3 to port 4 via an internal channel and exits port 4 of valve 627 via capillary tubing 632 before passing out to waste bottle 622.

It will be noted that in the "Flush" mode, the $V_x$ inlet capillary tubing 628 and the $V_x$ outlet capillary tubing 631 are joined by an internal channel between ports 2 and 3 of valve 627, closing the cross flow into a circle and thereby facilitating cleaning of the filtration membrane. This flushing of the channel need not be performed after every run, but can be performed whenever the need arises. Also, in "Flush" mode, cross-flow inlet port 1 of valve 627 is connected via an internal channel to port 6, so that the cross-flow fluid stream passes out of port 6 and through capillary tubing 633 to waste bottle 622.

The channel flow stream and the injected analyte sample are controlled by a computer 635 in FIG. 6 connected by a communication cable 636 to the $V_z$ pump 608.

The crossflow rate can be controlled either by restrictive capillary tubing 631 or 632 or by the choice of the porosity of the ultrafiltration membrane. The channel flow rate into and through the detectors is controlled by pieces of small-diameter capillary tubing 617, 619, and 621. This capillary tubing can be made from any material, but most commonly is made from stainless steel, poly(etheretherketone), PTFE, or titanium. The tubing diameters most commonly used are 0.254 mm (0.010"), 0.178 mm (0.007"), 0.127 mm (0.005"), 0.102 mm (0.004"), and 0.076 mm (0.003").

Stopless and splitless relaxation is achieved by the use of the conditions of the present invention as illustrated in FIG. 6. According to the process of the present invention, a relatively low channel flow rate $V_z$ is employed, so that the axial velocity of the entering analyte sample is minimized while maintaining a sufficient flow rate to establish a Poiseuille flow velocity profile. In addition, a relatively large crossflow rate $V_x$ is employed, so that relaxation of the analyte to its equilibrium position against the membrane occurs rapidly in relation to the sample's slow axial velocity. The sample pulse is introduced via the autoinjector 612 into the channel flow inlet carrier stream which enters the inlet end 614 of the channel 615. In this fashion, the relaxation process for the analyte upon entering the channel becomes effectively instantaneous, relative to both the analytical time scale and the diffusional time scale. That is, because the volumetric cross flow rate is large compared with the volumetric channel flow rate, analyte particles entering the channel drop to their equilibrium positions against the ultrafiltration membrane very rapidly, before the particles have sufficient time to travel either convectively or diffusively too far into the channel. No stopping or reversing of the channel flow takes place; instead, relaxation of the sample occurs within a few seconds under the relatively strong influence of the crossflow field entering the channel 615 from crossflow inlet port 629. This sample relaxation process is referred to as stopless and splitless relaxation, and is distinct from hydrodynamic relaxation. The analyte sample then separates out into its component bands as it travels down the length of channel 615, and these component bands exit from the channel 615 at the channel flow outlet port 616 and flow through tubing 617 into the detector train, possibly consisting of a light-scattering detector 618 and a UV or other detector 620. The sample then passes out from the detectors, where it can either pass into the waste bottle 622 or be collected with an ordinary HPLC or LC fraction collector.

Thus, the improved process of the present invention consists of several simultaneous processes, including the minimization of the thickness of the channel spacer commensurate with the size and properties of the analyte, the maximization of the crossflow field without driving the analyte too hard into the ultrafiltration membrane, the minimization of the channel flow rate commensurate with maintaining a useful Poiseuille flow velocity profile, the reduction of the diameter of the incoming $V_z$ inlet tubing to a sufficiently narrow bore tubing to restore or maximize the momentum imparted to the entering analyte stream, the use of two constant and uninterrupted fluid flows $V_z$ and $V_x$ through the channel, injection of the sample directly into the channel flow $V_z$ without subsequently stopping either flow for the purpose of relaxing the sample in the cross flow, and minimizing the area of the membrane which is covered by the entering particles, i.e. the width of the analyte peak, leading to an increase in resolution of the subsequent fractionation. The increased linear velocity of the incoming analyte sample, combined with the thinner channel, provides highly efficient and rapid relaxation, leading directly to increased resolution and obviating the need for stopping or reversing either flowstream. This renders unnecessary any of the currently-employed relaxation methods, stop-flow relaxation, hydrodynamic relaxation, or reversed-flow focussing, and also avoids the artifactual induction of aggregation seen with hydrodynamic relaxation and reversed-flow focussing. Thus, the improved flow FFF method of the present invention provides a higher degree of confidence that the analyte distribution measured using the present invention will accurately reflect the actual distribution of the sample.

After the stopless and splitless fractogram has been obtained, the improved calculation process of the present invention provides a means for calibrating the channel width w without reference to any void peaks in the fractogram. As an example of such a calibration calculation performed with hen egg-white lysozyme and BSA, in which a 127 μm spacer was used and the difference in retention times $(t_2-t_1)$ was found to be 6.284 min, Equation 3 gave, $$w = \sqrt{\left(\frac{6.284 \text{ min} \cdot 60 \frac{\text{sec}}{\text{min}}}{1.44 \times 10^{-7} \text{ cm}}\right)\left(\frac{2 \cdot \left(1.38 \times 10^{-16} \frac{\text{g} \cdot \text{cm}^2}{\text{s}^2 \cdot \text{K}}\right)}{2.9295 \times 10^{-2} \frac{\text{g}}{\text{cm} \cdot \text{s}}}\right)\left(\frac{0.0462}{3.9538}\right)}$$

$$= 9.24 \times 10^{-3} \text{ cm} = 92.4 \text{ μm}.$$

The channel volume can then be calculated from this channel width w using the equation V=area·width. The channel area of one specific split-inlet model FISI-1000 flow FFF channel is 53.5 cm², so the channel volume can be calculated, $$V = (53.5) \cdot (9.24 \times 10^{-3}) = 0.494 \text{ cm}^3 = 494 \text{ μL}.$$

At a channel flow rate $V_z$ of 46.2 μL/min, the void time $t_0$ can also be calculated, $$t_0 = \frac{V_0}{V_z} = \frac{494}{46.2} = 10.7 \text{ min.}$$

It will be apparent to one skilled in the art that the foregoing procedure is not significantly more difficult to practice than is ordinary HPLC or LC, with the only important differences being the use of the extra cross-flow pump 608, the use of the extra valve 627, and the associated extra tubing. This illustrates one of the prime objects of the present invention, namely, that the improved flow FFF process be capable of being performed on conventional, commercially-available HPLC and LC equipment by persons skilled in the art. This frees the flow FFF technique from the requirement for complicated, expensive, and dedicated hardware and software, and permits the improved flow FFF process to be performed in almost any laboratory which possesses an HPLC or LC instrument.

Figure 7:
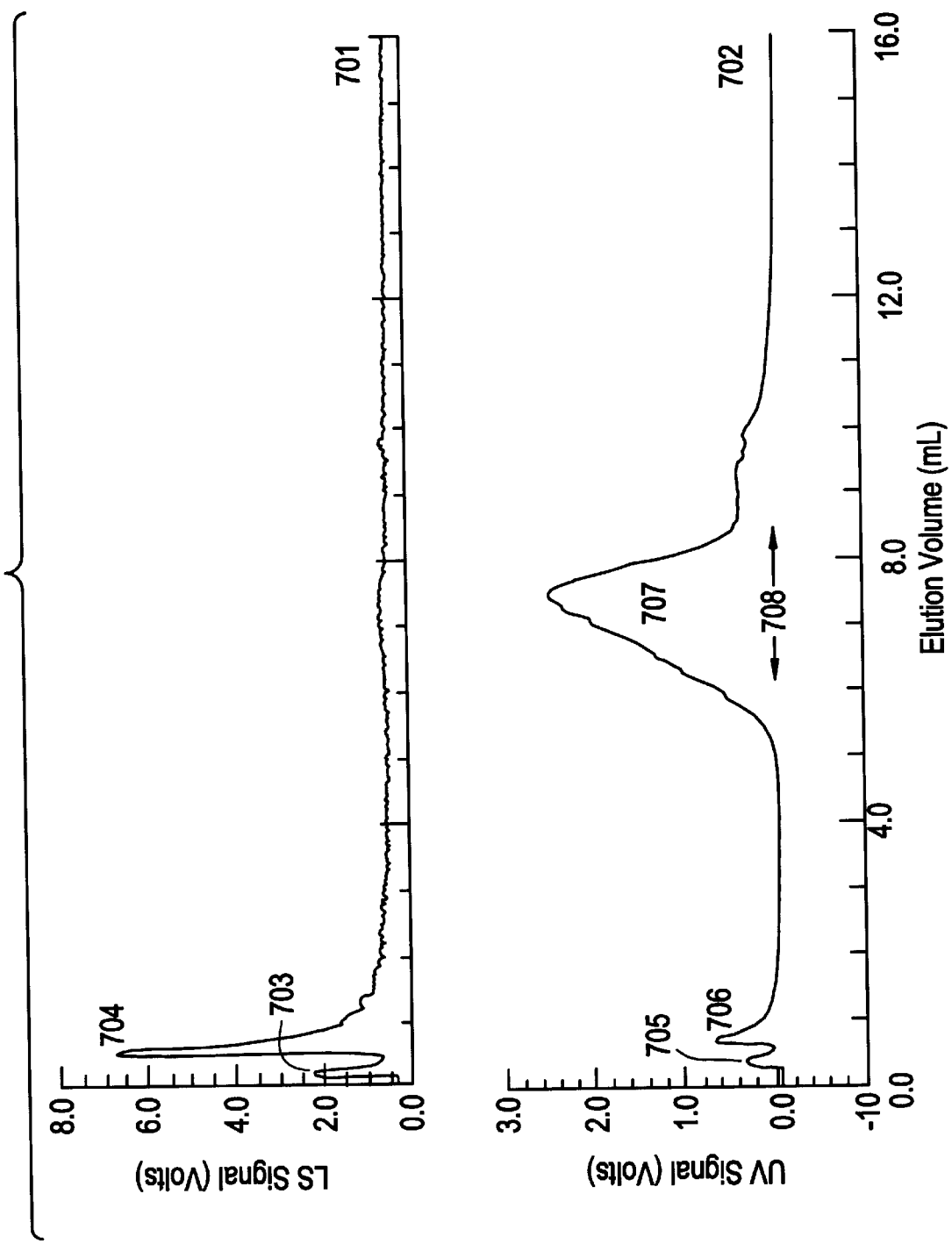
FIG. 7 shows a record of a fractogram containing a record of the 90° light-scattering and UV signals as a function of the elution volume obtained by subjecting the protein bovine serum albumin (BSA) to the conventional stopped-flow flow FFF method.

FIG. 7 provides a record of the signals obtained as a function of the elution volume by subjecting 250 $\mu$g of the protein BSA contained in a volume of 5.0 $\mu$L of the aqueous PBS carrier to the conventional stop-flow flow FFF procedure with $V_z$=0.485 mL/min and $V_x$=3.44 mL/min, for a flux ratio $V_x/V_z$ of 20.6. Plot 701 contains the 90° light-scattering voltages collected by the light-scattering detector 618 in FIG. 6 and plot 702 of FIG. 7 contains the UV voltages collected by the UV detector 620 in FIG. 6. The two LS peaks 703 and 704 in FIG. 7 appearing between elution volumes of 0 and 1.0 mL represent the baseline disturbances typical of the stop-flow technique, and may consist of unrelaxed material which exits from the flow FFF channel rather than being fractionated. The height of the UV peaks 705 and 706 in FIG. 7 show that this fraction of the sample is not negligible compared with the area 707 under the main UV peak. The ratio of the LS signal to the corresponding UV signal for each slice implies very large objects and suggests that biasing of the sample is taking place. Because of the enormous difference in properties such as molecular mass and size, data from these rapidly-eluting early peaks such as 703–706 are normally not included in the data representing the main bolus of analyte, so that the properties calculated for the main bolus do not necessarily represent all of the injected sample. The width 708 of the UV peak for the BSA monomer is about 3.8 mL (roughly 7.8 minutes), confirming the relatively poor resolution obtained with the conventional stop-flow flow FFF procedure.

Figure 8:
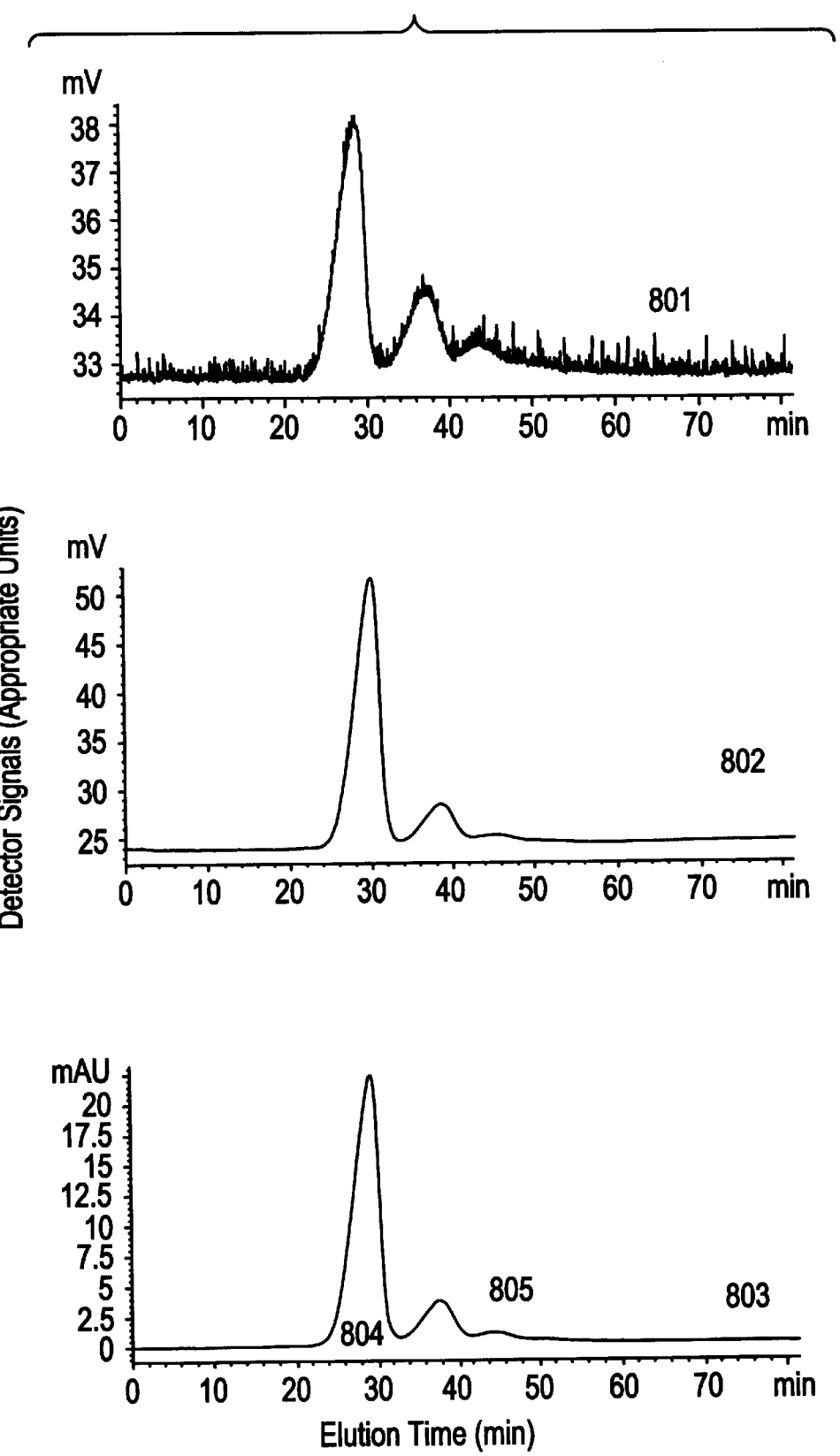
FIG. 8 shows a record of three detector signals, the 90° light-scattering (LS), refractive index (RI), and UV traces, obtained as a function of the elution time by subjecting the protein BSA to the new stopless and splitless flow FFF method.

The present invention describes a set of procedures intended to ensure sufficiently mild hydrodynamic and fluidic conditions to enable the use of the even the most sensitive detectors, while optimizing several other factors. FIG. 8 contains a plot 801 of the 90° light-scattering voltage of the protein bovine serum albumin (BSA) as a function of the elution time obtained by subjecting 49.5 $\mu$g of the protein BSA contained in 2.0 $\mu$L of the carrier to the new stopless and splitless flow FFF method. The record 802 of the RI voltages and the record 803 of the UV voltages as a function of the elution time used in the calculation of the molecular mass plot 801. The absence of pre-peaks in any of the three fractograms is one major advantage of the present invention. When the new stopless flow FFF procedure is employed, all of the sample elutes in the main bolus without any baseline disturbances. The width 804 of the UV peak for the BSA monomer is about 1.84 mL (roughly 10 minutes), is less than half of the stop-flow elution volume of 3.8 mL obtained from the UV trace 702 shown in FIG. 7, confirming the excellent resolution obtained in the absence of a stop-flow period. The fraction 805 of the protein eluting from about 32 minutes to about 58 minutes consists of protein aggregates, and the three detector signals 801–803 can be used to calculate the molecular mass distribution and other useful properties of the protein.

Figure 9:
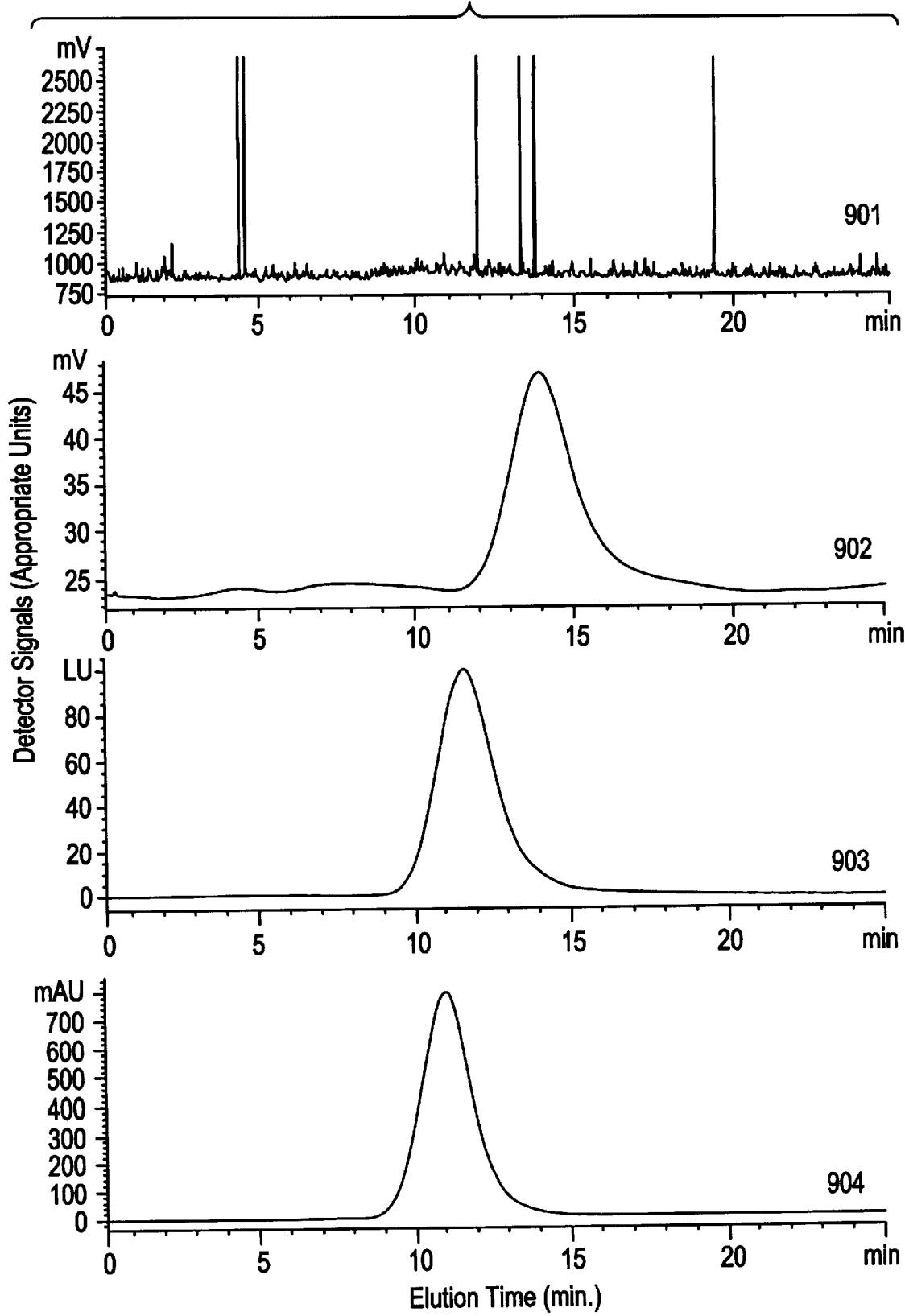
FIG. 9 shows a record of four detector signals, the 90° light-scattering (LS), refractive index (RI), fluorescence (FL), and UV traces, obtained as a function of the elution time by subjecting the protein hen egg-white lysozyme to the new stopless and splitless flow FFF method.

FIG. 9 contains a record of the four detector signals obtained by subjecting 5 $\mu$g of the protein hen egg white lysozyme, a small protein of molecular mass 14.3 kDa, to the new stopless and splitless flow FFF method. The 90° light-scattering voltages 901 (collected by the light-scattering detector 618 in FIG. 6), the RI voltages 902 (collected by the RI detector 620 in FIG. 6), the FL voltages 903 (collected by the FL detector 620 in FIG. 6), and the UV voltages 904 (collected by the WV detector 620 in FIG. 6) are shown as a function of the elution time. Despite it's small magnitude, the LS signal 901, in combination from one or more of the other detectors, can be used to calculate the molecular mass distribution and other properties of the protein. Using the new stopless flow FFF procedure, all of the sample elutes in the main bolus without any baseline disturbances.

Figure 10:
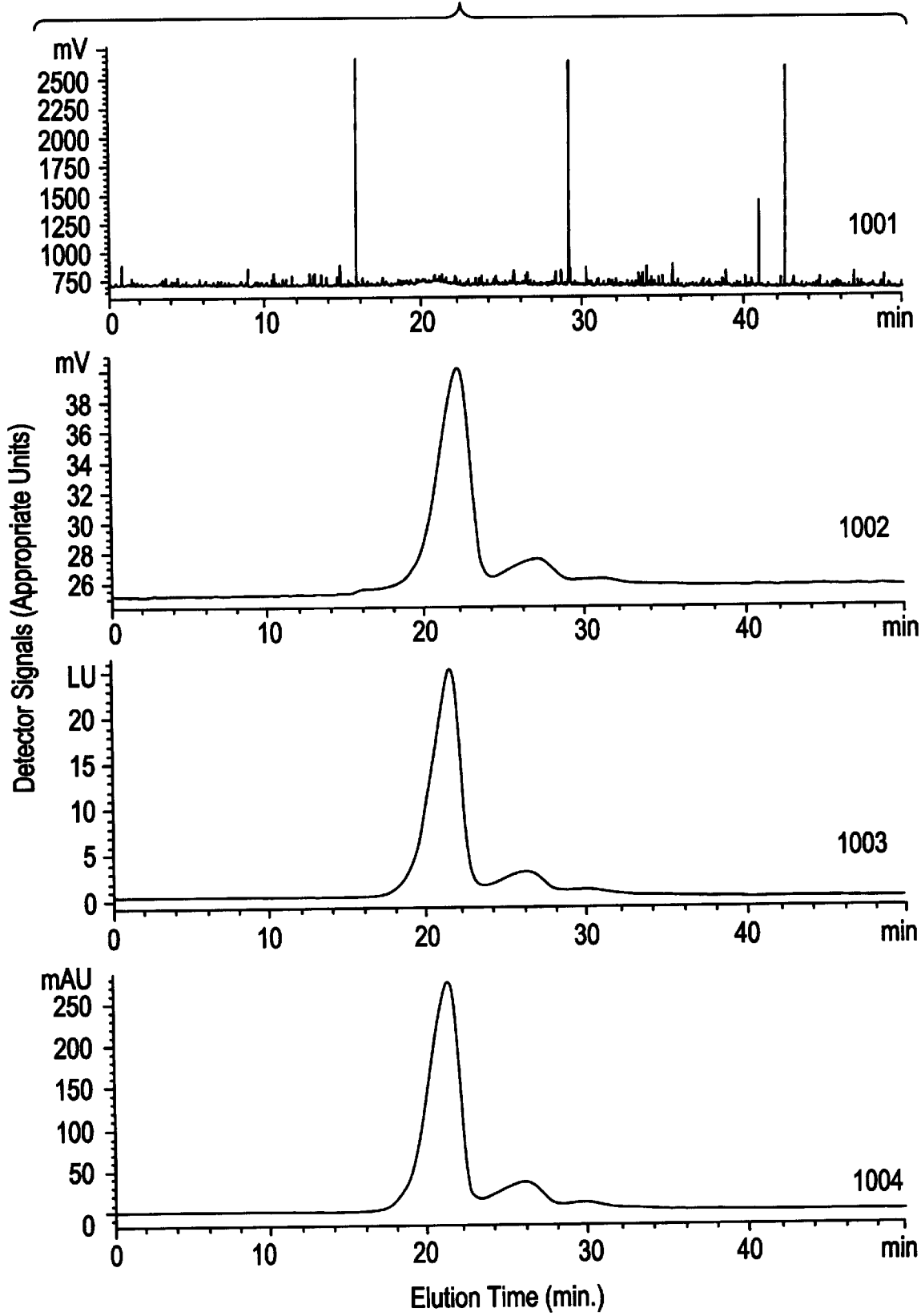
FIG. 10 shows a record of four detector signals, the 90° light-scattering (LS), refractive index (RI), fluorescence (FL), and UV traces, obtained as a function of the elution time by subjecting the protein BSA to the new stopless and splitless flow FFF method using a trapezoidal channel shape similar to 416 in FIG. 4.

FIG. 10 contains a record of the four detector signals obtained by subjecting 40 $\mu$g of the protein BSA contained in 4.0 $\mu$L of the carrier to the new stopless and splitless flow FFF method in a channel having walls tapered as illustrated by channel spacer 416 in FIG. 4. The 90° light-scattering voltages 1001 (collected by the light-scattering detector 618 in FIG. 6), the RI voltages 1002 (collected by the RI detector 620 in FIG. 6), the FL voltages 1003 (collected by the FL detector 620 in FIG. 6), and the UV voltages 1004 (collected by the UV detector 620 in FIG. 6) are shown as a function of the elution time of the protein. Once again, with the new stopless flow FFF procedure all of the sample elutes in the main bolus without any baseline disturbances, and the LS signal 1001, in combination from one or more of the other detectors, can be used to calculate the molecular mass distribution and other properties of the protein.

Figure 11:
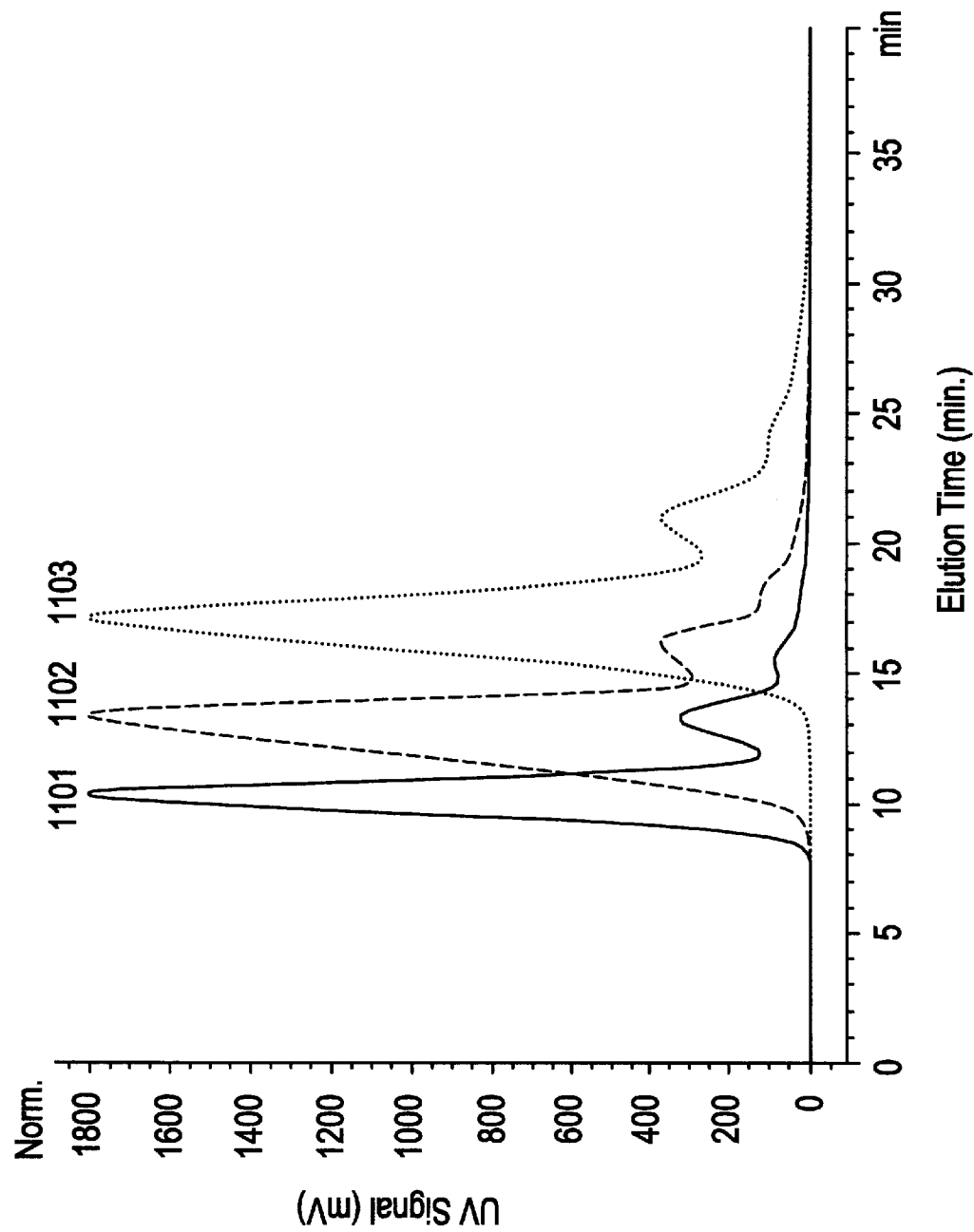
FIG. 11 shows a record of three UV detector signal traces for the protein BSA obtained using the new stopless and splitless flow FFF method with three different levels of the flux ratio $V_x/V_z$ under a variety of operating conditions.

FIG. 11 shows a series of three elution profiles obtained with the protein BSA using the new stopless and splitless flow FFF method with a symmetrical channel at a total flux of 4.0mL/min and different levels of the flux ratio, $V_x/V_z$. The UV elution profile 1101 was obtained with 40 $\mu$g of BSA contained in 4.0 $\mu$L of the carrier at a flux ratio $V_x/V_z$ of 32.3. UV elution profile 1102 was obtained with 50 $\mu$g of BSA contained in 2.0 $\mu$L of the carrier at a flux ratio of 46.6. UV elution profile 1103 was obtained with 30 $\mu$g of BSA contained in 3.0 $\mu$L of the carrier at a flux ratio of 86.0. It can be seen that the best results, including maximal resolution, are obtained by injecting modest analyte loads in reasonably small volumes. The fractogram at each of these flux ratios shows partially resolved peaks for the protein monomer, dimer, and trimer. This figure shows clearly that high-resolution flow FFF fractionation can be realized by employing the new stopless and splitless relaxation procedure and flow conditions to produce separations and spectroscopic data which are otherwise not achievable when stopping, splitting, or reversing the channel flow.

EXAMPLE 1

A model FISI-1000 symmetrical, split-outlet flow FFF channel, similar to that shown schematically in FIG. 3 but having an additional outlet for use as either an inlet or an outlet splitter, was purchased commercially from FFFractionation LLC (Salt Lake City, Utah) and used as received except that the original 0.254 $\mu$m (0.010") Mylar channel spacer was replaced with a 0.127 $\mu$m (0.005") thick Mylar channel spacer with a parallel-walled channel hole of type 401 in FIG. 4 cut out from it, and the connection to the inlet splitter was plugged and not used. The sample material is introduced through a short length of flanged 254 $\mu$m (0.010") PTFE channel flow inlet tubing inserted into the above system by means of a hole drilled through the Lucite housing block and the ceramic frit at the inlet tip of the frit chamber. A similar hole drilled through the same Lucite housing block and the ceramic frit at the outlet tip of the channel contains another piece of flanged 254 $\mu$m (0.010") PTFE tubing comprising the channel flow outlet. The resulting flow FFF channel in which the separation took place was 28.5 cm in tip-to-tip length, and 2.0 cm in breadth, yielding a geometrical channel volume of approximately 0.5 mL. Sandwiched inside the channel was a 3 kDa Amicon (Beverly, Mass.) YM3 regenerated cellulose membrane which served as the accumulation wall of the channel. Beneath the membrane was a ceramic frit, approximately 0.60 cm thick, with a 5 μm average pore size. The frit was mounted in a Lucite block directly above a thin chamber (the outlet crossflow chamber) designed to collect the crossflow as it emerged through the frit. Sandwiched immediately above the channel, and serving as the depletion wall, was a second, identical slab of ceramic frit mounted in a Lucite block similar to the first. A thin (0.30 cm) chamber was cut into the block above the frit identical to that on the outlet crossflow chamber and extended to within 0.25 cm of the sample inlet port. The sample material is introduced through the short length of flanged 254 μm (0.010") PTFE channel flow inlet tubing joined to the channel flow poly (etheretherketone) (PEEK) capillary tubing via low-pressure ¼-28 LC fittings, depositing the sample onto the inlet tip of the flow FFF channel. After traversing the channel axially under the influence of the cross-flow field, the sample bands elute through the short length of flanged 254 μm (0.010") PTFE channel flow outlet tubing joined to additional poly (etheretherketone) (PEEK) capillary tubing via low-pressure ¼-28 LC fittings.

A Hewlett-Packard 1050-series HPLC metering pump was used to introduce the channel flow $V_z$ into the channel through the channel flow inlet. Aliquots of the analyte were introduced into this channel flow stream by means of a Hewlet-Packard 1100-series HPLC autosampler, which held the analyte cooled to 4°. A second, identical Hewlett-Packard 1050-series HPLC metering pump was used to introduce the crossflow stream into the channel through the crossflow inlet frit. After traversing the channel width, the cross flow exited through the crossflow outlet frit and passed through a section of capillary tubing to a waste container. Components emerging from the channel were detected by a Wyatt Technology (Santa Barbara, Calif.) miniDawn light-scattering photometer bearing three sensing photodiodes placed at 45°, 90°, and 135° relative to the incident 10-mW laser beam operating at 690-nm, and by a Hewlett-Packard 1050-series UV/Vis absorption detector operating at 280 nm, and by a Hewlett-Packard 1047A refractive-index (RI) detector. Data were collected into Hewlett-Packard's ChemStation software, processed, and printed to yield the results shown in FIG. 8.

The carrier fluid used in this study was aqueous phosphate-buffered saline (PBS), prepared by dissolving 150 mM sodium chloride, 10 mM sodium phosphate, and 0.0002% sodium azide in Milli-Q-purified water and adjusting the pH to 7.40 using dilute aqueous NaOH and/or dilute aqueous HCl. The PBS buffer was degassed and vacuum filtered through a 0.02 μm Whatman Anodisc filter and placed into a helium-sparged reservoir on the HPLC system. An online Hewlett-Packard 1100-series vacuum degasser removed residual helium. The system was operated at an ambient laboratory temperature of approximately 23°±2° C.

The flow FFF system was assembled and the flow FFF channel flushed with PBS buffer and then connected as shown in FIG. 6. The $V_x$ valve 627 in FIG. 6 was placed in "run" mode and the channel flow rate $V_z$ eluting from the RI detector 620 in FIG. 6 was measured by collecting the effluent for a precisely-timed interval and weighing the obtained mass of carrier on an analytical balance. The flow rate of the $V_z$ pump 607 in FIG. 6 was then set to $V_z$=0.184 mL/min, and the flow rate on the $V_x$ pump 608 in FIG. 6 was set to $V_x$=3.783 mL/min, for a flux ratio $V_x/V_z$=86.0. After establishing a quiet baseline in the LS detector 618 and UV and RI detectors 620 in FIG. 6, the autoinjector 612 in FIG. 6 was programmed to inject a 2.0 μL (50 μg) aliquot of the protein BSA (Sigma, St. Louis, Mo.) dissolved in the aqueous PBS carrier. The data collected from the LS, RI, and UV detectors comprise FIG. 8.

EXAMPLE 2

The flow FFF analytical system configured as described in Example 1 was modified as follows. The Wyatt Technology (Santa Barbara, Calif.) miniDawn light-scattering photometer was replaced with a Precision Detectors (Franklin, Mass.) model PD2020 light-scattering photometer containing two sensing photodiodes placed at 15° and 90° relative to the incident 70 mW laser beam operating at 809 nm, and a Hewlett-Packard 1100-series fluorescence detector was added after the UV absorbance detector and before the RI detector. The order of the detectors was thus LS, UV, FL, and RI, after which the sample flowed into a waste container. Only the 90° LS signal was collected from the PD2020 LS detector into the Hewlett-Packard ChemStation software, and not the 15° LS signal, along with the UV signal at 280 nm, the fluorescence signal with EX32 280 nm and EM=350 nm, and the RI signal. Another 3 kDa Amicon (Beverly, Mass.) YM3 regenerated cellulose membrane served as the accumulation wall of the channel. The inline channel flow filter was a 13-mm Pall Filtron Nova 1-kDa ultrafiltration membrane, and the inline crossflow filter was a 47 mm Pall Filtron Nova 1 kDa ultrafiltration membrane. The same pH 7.40 PBS carrier fluid was again degassed and vacuum filtered through a 0.02 μm Whatman Anodisc filter and placed into a helium-sparged reservoir on the HPLC system. An online Hewlett-Packard 1100-series vacuum degasser removed residual helium. The analyses were conducted at an ambient laboratory temperature of approximately 23°±2° C.

The flow FFF system was assembled and flushed with PBS buffer as described in Example 1. The $V_x$ valve 627 in FIG. 6 was placed in "run" mode and the channel flow rate $V_z$ eluting from the RI detector 620 in FIG. 6 was measured by collecting the effluent for a precisely-timed interval and weighing the obtained mass of carrier on an analytical balance. The flow rate of the $V_z$ pump 607 in FIG. 6 was then set to $V_z$=0.120 mL/min, and the flow rate on the $V_x$ pump 608 in FIG. 6 was set to $V_x$=3.880 mL/min, for a total flux of 4.0 mL/min and a flux ratio $V_x/V_z$=32.3. After establishing a quiet baseline in the LS detector 618 and UV and RI detectors 620 in FIG. 6, the autoinjector 612 in FIG. 6 was programmed to inject a 40 μg aliquot of the protein BSA (Sigma, St. Louis, Mo.) dissolved in 4.0 μL of the aqueous PBS carrier. The data collected from the UV detector were processed and printed to yield the signal 1101 shown in FIG. 11.

With the $V_x$ valve 627 in FIG. 6 placed in "run" mode, the channel flow rate $V_z$ eluting from the RI detector 620 in FIG. 6 was again measured by collecting the effluent for a precisely-timed interval and weighing the obtained mass of carrier on an analytical balance. The flow rate of the $V_z$ pump 607 in FIG. 6 was then set to $V_z$=0.046 mL/min, and the flow rate on the $V_x$ pump 608 in FIG. 6 was set to $V_x$=3.954 mL/min, for a total flux of 4.0 mL/min and a flux ratio $V_x/V_z$=86.0. After establishing a quiet baseline in the LS detector 618 and UV and RI detectors 620 in FIG. 6, the autoinjector 612 in FIG. 6 was programmed to inject a 30 μg aliquot of the protein BSA (Sigma, St. Louis, Mo.) dissolved in 3.0 μL of the aqueous PBS carrier. The data collected from the UV detector were processed and printed to yield the signal 1103 shown in FIG. 11. The autoinjector 612 in FIG. 6 was then programmed to inject a 5-μg aliquot of the protein hen egg-white lysozyme (Sigma, St. Louis, Mo.)

dissolved in 2.0 µL of the aqueous PBS carrier. The data collected from the LS, RI, FL, and UV detectors were processed and printed to yield the results shown in FIG. 9.

EXAMPLE 3

The flow FFF analytical system configured as described in Example 2 was further modified as follows. The parallel-walled channel spacer similar to spacer 401 in FIG. 4 was replaced with a tapered channel spacer similar to spacer 416 in FIG. 4, with the wide end of the channel at the channel-flow inlet end and the pointed end of the channel at the channel-flow outlet end of the channel. Another 3 kDa Amicon (Beverly, Mass.) YM3 regenerated cellulose membrane was installed as the accumulation wall of the channel. A similar batch of pH 7.40 PBS carrier fluid was again degassed and vacuum filtered through a 0.02 µm Whatman Anodisc filter and placed into a helium-sparged reservoir on the HPLC system, from which an online Hewlett-Packard 1100-series vacuum degasser removed residual helium. The analyses were conducted at an ambient laboratory temperature of approximately 23°±2° C.

The tapered-channel flow FFF system was assembled and flushed with PBS buffer as described in Example 2. The $V_x$ valve 627 in FIG. 6 was placed in "run" mode and the channel flow rate $V_z$ eluting from the RI detector 620 in FIG. 6 was measured by collecting the effluent for a precisely-timed interval and weighing the obtained mass of carrier on an analytical balance. The flow rate of the $V_z$ pump 607 in FIG. 6 was then set to $V_z$=0.153 mL/min, and the flow rate on the $V_x$ pump 608 in FIG. 6 was set to $V_x$=2.347 mL/min, for a flux ratio $V_x/V_z$=15.3. After establishing a quiet baseline in the LS detector 618 and UV and RI detectors 620 in FIG. 6, the autoinjector 612 in FIG. 6 was programmed to inject a 40 µg aliquot of the protein BSA (Sigma, St. Louis, Mo.) dissolved in 4.0 µL of the aqueous PBS carrier. The data collected from the LS, RI, FL, and UV detectors were processed and printed to yield the results shown in FIG. 10.

EXAMPLE 4

The flow FFF analytical system configured as described in Example 1 was modified as follows. The Wyatt Technology miniDawn light-scattering photometer was replaced with an Hitachi Instruments (San Jose, Calif.) model L-7480 fluorescence detector containing one sensing photodiode placed at 90° relative to the incident light beam emanating from a xenon lamp. The fluorescence detector was operated in Rayleigh light-scattering mode with EX=488 nm and EM=458 nm. The parallel-walled Mylar 0.005" channel spacer similar to spacer 401 in FIG. 4 was replaced with a similar parallel-walled polyester 0.005" channel spacer. Another 3 kDa Amicon (Beverly, Mass.) YM3 regenerated cellulose membrane was installed as the accumulation wall of the channel. A similar batch of pH 7.40 PBS carrier fluid was again degassed and vacuum filtered through a 0.02 µm Whatman Anodisc filter and placed into a helium-sparged reservoir on the HPLC system, from which an online Hewlett-Packard 1100-series vacuum degasser removed residual helium. The analyses were conducted at an ambient laboratory temperature of approximately 23°±2° C. The components emerging from the channel were detected first by the Hitachi L-7480 fluorescence detector operated in LS mode, and by a Hewlett-Packard 1050-series UV/Vis absorption detector operating at 280 nm, and by a Hewlett-Packard 1047A refractive-index (RI) detector. The same pH 7.40 PBS carrier fluid was again degassed and vacuum filtered through a 0.02 µm Whatman Anodisc filter and placed into a helium-sparged reservoir on the HPLC system. An online Hewlett-Packard 1100-series vacuum degasser removed residual helium. The analyses were conducted at an ambient laboratory temperature of approximately 23°±2° C.

The flow FFF system was assembled and the flow FFF channel flushed with PBS buffer and then connected as shown in FIG. 6. The $V_x$ valve 627 in FIG. 6 was placed in "run" mode and the channel flow rate $V_z$ of pump 607 in FIG. 6 was set to $V_z$=0.084 mL/min, and the flow rate on the $V_x$ pump 608 in FIG. 6 was set to $V_x$=3.916 mL/min, for a inlet flux ratio $V_x/V_z$=46.6. The capillary tubing leading out from the channel flow outlet and the crossflow outlet were then adjusted, the channel flow rate $V_z$ eluting from the RI detector 620 in FIG. 6 was measured at 0.145 mL/min, and the crossflow rate $V_x$ eluting from the channel through capillary tubing 631 in FIG. 6 was measured at 3.82 mL/min. These lower $V_x$ and $V_z$ inlet flow rates and higher $V_x$ and $V_z$ outlet flow rates thus established a set of "semi-symmetrical" channel operating conditions, in which a channel flow-rate gradient existed across the axial dimension of the channel, and a cross flow-rate gradient existed across the width dimension of the channel. After establishing a quiet baseline in the LS detector 618 and UV and RI detectors 620 in FIG. 6, the autoinjector 612 in FIG. 6 was programmed to inject a 50 µg aliquot of the protein BSA (Sigma, St. Louis, Mo.) dissolved in 2.0 µL of the aqueous PBS carrier. Data were collected from the Hitachi L-7480, RI, FL, and UV detectors into Hewlett-Packard's ChemStation software, and the UV signal was processed and printed to yield the signal 1102 shown in FIG. 11.

While the present invention has been shown and described in its preferred embodiment and in certain specific alternative embodiments, those skilled in the art will recognize from the foregoing discussion that various changes, modifications, and variations may be made thereto without departing from the spirit and scope of the invention as set forth in the claims. In particular, it will be apparent to one skilled in the art that many other chromatographic components, such as additional valves, injectors, detectors, fraction collectors, degassers, and other such components, can also be used in conjunction with the present invention, depending on the application and the nature of the analyte sample. Hence, the embodiment and specific dimensions, materials, and the like are merely illustrative and do not limit the scope of the invention or the claims herein.

What is claimed is:

1. A flow field-flow fractionation process for the separation of an analyte, said process comprising:

a) employing a channel spacer of the minimal thickness to minimize the axial dispersion of an entering analyte sample and to maximize the high-velocity component of the relaxation process;

b) employing a sufficiently high crossflow rate $V_x$ to aid in rapidly relaxing the entering analyte sample and to maximize the linear crossflow velocity ratio $U_x/U_z$ while avoiding artifactual adhesion of the analyte to the ultrafiltration membrane;

c) employing as the accumulation wall an ultrafiltration membrane which is sufficiently tight-pored to provide enough pressure in the channel to maintain a constant cross-sectional area throughout the axial length of the channel, while avoiding absorption of the analyte to the ultrafiltration membrane;

d) employing a sufficiently small channel flow rate $V_z$ so as to minimize the linear channel flow velocity $U_z$ to ensure the rapid and efficient relaxation of the incoming analyte sample against the ultrafiltration membrane and to maximize the linear crossflow velocity ratio $U_x/U_z$ while maintaining a sufficiently large linear channel flow velocity $U_z$ to ensure the presence of a Poiseuille flow velocity distribution within the channel sufficient to effect a flow FFF separation;

e) introducing an analyte sample in a minimal volume of fluid and in the single channel flow stream, rather than into a separate or dedicated substream;

f) continuing both the channel flow and the crossflow streams uninterrupted after the introduction of the sample into the channel, and not introducing any additional substreams into the channel for the purpose of hydrodynamically relaxing the sample.

2. A process as in claim 1 in which a planar channel is employed.

3. A process as in claim 1 in which a cylindrical or annular channel is employed.

4. A process as in claim 1 in which the flow FFF channel is operated in symmetrical mode.

5. A process as in claim 1 in which the flow FFF channel is operated in asymmetrical mode.

6. A process as in claim 1 in which a channel spacer with parallel side walls and triangular endpieces is employed.

7. A process as in claim 1 in which a channel spacer with parallel side walls and one or more rounded endpieces is employed.

8. A process as in claim 1 in which a tapered channel spacer with triangular endpieces is employed.

9. A process as in claim 1 in which a tapered channel spacer with one or more rounded endpieces is employed.

10. A process as in claim 1 in which the channel spacer tapers to a point.

11. A process as in claim 1 in which the analyte is selected from the group consisting of proteins, nucleic acids, macromolecules, or vesicles.

* * * * *